US012364747B2

(12) United States Patent
Dhere et al.

(10) Patent No.: US 12,364,747 B2
(45) Date of Patent: Jul. 22, 2025

(54) STABILIZED LIVE ATTENUATED INFLUENZA VACCINE COMPOSITIONS

(71) Applicant: SERUM INSTITUTE OF INDIA PVT LTD., Pune Maharashtra (IN)

(72) Inventors: Rajeev Mhalasakant Dhere, Pune Maharashtra (IN); Leena Ravindra Yeolekar, Pune Maharashtra (IN); Milan Shomenath Ganguly, Pune Maharashtra (IN); Parikshit Dharampal Tyagi, Pune Maharashtra (IN); Umesh Gorakh Sagar, Pune Maharashtra (IN); Swapnil Prabhakar Narale, Pune Maharashtra (IN); Yashodhan Dilip Anaspure, Pune Maharashtra (IN); Sham Ramdas Tupe, Pune Maharashtra (IN)

(73) Assignee: Serum Institute of India Private Limited, Pune Maharashtra (IN)

( * ) Notice: Subject to any disclaimer, the term of this patent is extended or adjusted under 35 U.S.C. 154(b) by 1011 days.

(21) Appl. No.: 17/429,965

(22) PCT Filed: Feb. 7, 2020

(86) PCT No.: PCT/IN2020/050121
§ 371 (c)(1),
(2) Date: Aug. 11, 2021

(87) PCT Pub. No.: WO2020/165912
PCT Pub. Date: Aug. 20, 2020

(65) Prior Publication Data
US 2022/0211837 A1    Jul. 7, 2022

(30) Foreign Application Priority Data
Feb. 15, 2019    (IN) .............................. 201921006071

(51) Int. Cl.
| | |
|---|---|
| *A61K 39/145* | (2006.01) |
| *A61K 9/00* | (2006.01) |
| *A61K 47/02* | (2006.01) |
| *A61K 47/18* | (2017.01) |
| *A61K 47/26* | (2006.01) |
| *A61K 47/42* | (2017.01) |
| *A61P 31/16* | (2006.01) |
| *A61K 39/00* | (2006.01) |

(52) U.S. Cl.
CPC .......... *A61K 39/145* (2013.01); *A61K 9/0019* (2013.01); *A61K 47/02* (2013.01); *A61K 47/183* (2013.01); *A61K 47/26* (2013.01); *A61K 47/42* (2013.01); *A61P 31/16* (2018.01); *A61K 2039/5254* (2013.01); *C12N 2760/16034* (2013.01)

(58) Field of Classification Search
CPC .................... A61K 39/145; C12N 2760/16034
See application file for complete search history.

(56) References Cited

FOREIGN PATENT DOCUMENTS

| WO | 2015124594 A1 | 8/2015 |
|---|---|---|
| WO | 2019014338 A1 | 1/2019 |

OTHER PUBLICATIONS

White, J. A., et al., 2016, Development of a stable liquid formulation of live attenuated influenza vaccine, Vaccine 34:3674-3683.*
Jessica A. White et al.; "Development of A Stable Liquid Formulation of Live Attenuated Influenza Vaccine"; Vaccine, Elsevier, Amsterdam, NL; vol. 34; No. 32; May 4, 2016; pp. 3676-3683.
Svetlana Shcherbik et al.; "Implementation of New Approaches For Generating Conventional Reassortants For Live Attenuated Influenza Vaccine Based on Russian Master Donor Viruses"; Journal of Virological Methods; Elsevier Bv, NL; vol. 227, Oct. 28, 2015; pp. 33-39.

* cited by examiner

*Primary Examiner* — Jeffrey S Parkin
(74) *Attorney, Agent, or Firm* — BakerHostetler

(57) ABSTRACT

The present disclosure provides compositions and methods for manufacturing and obtaining a live attenuated Influenza vaccine (LAIV) composition that can be delivered intranasally to provide protection against influenza virus infection. Said LAIV strains are based on cold adapted, temperature sensitive and attenuated phenotypes of master donor viruses (MDVs) containing the surface glycoprotein genes of the wild type pandemic or seasonal influenza strains. Also, said LAIV strains are further adapted to grow in MDCK cells (Madin Darby canine kidney cells). The use of eggs is avoided in large scale vaccine manufacturing. The purification process is devoid of chromatography steps. The said LAIV composition includes one or more live attenuated influenza vaccine virus and is devoid of polymers and surfactants.

22 Claims, 13 Drawing Sheets

Stability @ 37° C (Stress Stability)

Y-axis: Virus Potency (EID$_{50}$/0.5ml)
X-axis: SQRT of Days

▲ A/17/California/2009/38
■ B/Texas/02/13-CDC $y = -0.9803x + 8.5623$
$R^2 = 0.8314$ $y = -0.8435x + 7.6646$
$R^2 = 0.7951$

STABILIZED LIVE ATTENUATED INFLUENZA VACCINE COMPOSITIONS

CROSS-REFERENCE TO RELATED APPLICATIONS

This application is a National Stage Application of International Patent App. No. PCT/IN2020/050121, filed Feb. 7, 2020, which claims priority to Indian Application No. 201921006071, filed Feb. 15, 2019, the entire disclosures of both of which are hereby incorporated by reference as if set forth in their entirety herein.

FIELD

The present disclosure relates to the field of viral vaccine manufacturing, more particularly, it relates to a live attenuated Influenza vaccine composition and the method of preparing the same. The present disclosure relates to a method for producing viruses, or viral antigens, produced by cell culture, to the viruses or viral antigens obtainable by this method and to vaccines which contain such viruses or viral antigens.

BACKGROUND

The background information herein below relates to the present disclosure but is not necessarily prior art.

Epidemics and pandemics caused by infectious agents have been occurring for centuries, causing major disruptions, with varying morbidity and mortality. The influenza virus has been one of the major players in the history of pandemics. Four influenza pandemics have occurred in the last century and at least 15 influenza pandemics have been recorded until now, with an estimated mortality of 50 million people in 1918-19 alone.

Vaccines play an important role in the control of virus spread, and the inactivated influenza vaccine (IIV) as well as live attenuated influenza vaccines (LAIV) have been in use for many years. The widely used parenterally administered inactivated influenza vaccines induce serum antibody responses effectively preventing influenza illness when circulating strains are antigenically matched to the vaccine. In contrast, live attenuated influenza vaccines (LAIVs) are administered intranasally, mimicking natural infection, induces both local and systemic humoral and cellular immune responses conferring protection to matched as well as drifted strains. In addition, the needle free application of LAIVs may lower the threshold for acceptance and thereby increase the influenza vaccine coverage.

To date, LAIVs are licensed in the US (since 2003), Europe (since 2010) Russia (since the 1980s) and India (since 2010). LAIVs are based on attenuated influenza A and B master donor viruses (MDVs) developed independently, but in essentially the same way, in the US and Russia in the 1960s. MedImmune seasonal and pandemic LAIV viruses are currently produced by the means of reverse genetics (RG). In contrast, Russian LAIVs are being produced by classical genetic reassortment in embryonated eggs. The Russian LAIV is recently being registered for use in China and Thailand.

The Russian LAIV consists of reassortant viruses, which contain hemagglutinin (HA) and in most instances the neuraminidase (NA) gene segments from circulating wild-type (WT) viruses of interest on a backbone of the remaining six internal protein genes (PB1, PB2, PA, NP, M and NS) derived from the (MDVs). The A/Leningrad/134/17/57 (H2N2) (Len-MDV) and B/USSR/60/69 MDVs are currently used in Russia as MDVs for LAIV. The MDVs contain mutations in multiple gene segments rendering them cold-adapted (ca), temperature sensitive (ts) and attenuated (att). The surface glycoproteins hemagglutinin (HA) and neuraminidase (NA) of contemporary strains are incorporated into these MDVs by reassortment. Their ca, ts and att phenotype indicates that LAIVs replicate at low temperatures, and stop replicating at higher temperatures (>38° C.) limiting replication to the upper respiratory tract. Compared to the MDVs used in the US, the Russian MDVs contain fewer mutations which are present at different sites of the gene segments, suggesting that they may be differently attenuated. Direct comparison in animals and man suggested that the Russian MDV and a single strain reassortant derived thereof were more immunogenic than the equivalents.

Over the years Russian LAIVs have been safely administered to more than 75 million people and have been shown to be safe with respect to attenuation (genetic stability) and transmission. Reversion to virulence (loss of the attenuated phenotype) has never been observed and is highly unlikely to occur as it would require reversion of multiple mutations in more than one gene segment. Neurovirulence of Russian LAIV viruses has never been reported and both MDVs and the reassortants derived thereof were shown not to have neurovirulent properties. Following the administration of an LAIV, there are no reports of serious adverse events associated with immunization except for self-limiting flu-like symptoms (runny nose, nasal congestion, sore throat, cough, headache and low grade fever) reported in rare cases. In addition to being safe, LAIVs have been shown to be efficacious in protection against illness caused by influenza virus infection. Immunity induced by LAIVs is broad and has been shown to protect against drifted strains. In children particularly, LAIVs were shown to be more effective in clinical protection and/or protection against culture confirmed influenza than inactivated influenza vaccine and also have been shown to confer herd immunity.

Like inactivated influenza vaccines, Russian LAIVs are produced using embryonated chicken eggs, with its own inherent disadvantages limited suppliers of vaccine quality and specific pathogen free eggs need advance ordering with a minimum of 4 months lead time before the eggs become available for large scale vaccine production. Specialized facility for egg incubation, harvesting etc in turn limit the capacity for rapid scale-up. The extended time required to produce egg-dependent vaccines might result in too few doses being available to counter a pandemic situation, such as occurred in 2009, or to stop a pandemic originating from a highly pathogenic Influenza virus. Therefore, the current vaccine production system would be inadequate to respond to an influenza pandemic, for which a novel rapid emergency vaccine manufacturing process is required. Theoretically, production of influenza vaccines in cell culture offers important advantages in case of pandemic. Manufacturing of the vaccine on large scale can be easily achieved using pre-existing tissue culture manufacturing units of other viral vaccines.

Control on availability of the substrate consistency and flexibility in production, rapid up-scaling, which is especially important in the case of a pandemic, independence from egg supply and maintenance of chicken flocks are the main advantages of tissue culture method. The egg shell is a porous structure and eggs are non-sterile on the outside. The manufacturing process for growing the influenza virus in eggs requires puncturing the egg shell for inoculation and open handlings for harvesting with an inherent risk of contamination. Furthermore cell culture is a more controlled system with defined cell culture media and validated cell banks in accordance with Good Manufacturing Practice (GMP), Therefore, attempts have been made to transfer production from eggs to cell culture.

Several cell lines are currently under investigation for cell culture-based influenza production, and the use of MRC-5 cells (Refer: de Ona et al. (1995) *J Clin Microbiol* 33:1948-49), HepG2 cells (Refer: Ollier et al. (2004) *J Clin Microbiol* 42(12):5861-5), LLC-MK2 cells (Refer: Schepetiuk & Kok (1993) *J Virol Methods* 42(2-3):241-50), Madin-Darby canine kidney (MDCK) cells (Refer: Tobita et al. (1975) *Med Microbiol Immunol (Berl)*. 162(1):9-14 and 23-27), African green monkey Vero cells (Refer: Monto et al. (1981) *J Clin Microbiol* 13(1): 233-235 and Govorkova et al. (1995) *J Infect Dis.* 172(1):250-3), and PER.C6 cells (Refer: Cox, R. J. et al.; Vaccine 2009, 27, 1889-1897) has been reported. Previously for MRC-5, WI-38 and FRhL cells, low to moderate titers of virus with titers equal or below 5.0 $\log_{10}$ $TCID_{50}$/ml have been reported, whereas for MDCK cells titers up to 6.7 $\log_{10}$ $TCID_{50}$/mL have been reported. While cell culture derived influenza vaccines (egg isolated influenza viruses adapted/optimized for growth in cell culture) are licensed in Europe (Optaflu Novartis; 2007) and US (Flucelvax Novartis; 2012), only a very small fraction of the influenza vaccines on the market is cell culture derived. This could be due inconsistent yields of influenza vaccine using cell culture production systems in combination with classical purification methods and cumbersome stabilization practice. Theoretical safety concerns related to the use of continuous cell lines such as MDCK cells have been raised related to their use in vaccine manufacture (VRBPAC, 2008). These concerns are primarily associated with residual cellular components (DNA and protein) in the vaccine drug product and are particularly relevant for live attenuated influenza vaccine (LAIV) products that are not inactivated nor undergo extensive biochemical purification as is the case for the traditional inactivated influenza vaccines. Two strategies have been undertaken to minimize these risks: cell line characterization and vaccine purification processing steps. A specific aspect of the purification process is to reduce the quantity and size of residual host cell DNA in the vaccine product. The manufacture of Optaflu Novartis (2007), include several steps to eliminate residual host cell DNA. These include cellulose sulfate ion-exchange chromatography that binds the influenza virus and allows DNA to pass through and a subsequent CTAB precipitation step that, inter alia, precipitates the DNA.

The previously reported purification processes are costly and time consuming as they employ one or more chromatography(s) from Hydroxyapatite, Affinity, Anion Exchange and Size Exclusion. The overall recovery of the virus has been reported to be suboptimal for routine vaccine production using chromatographic methods. Furthermore, circulating influenza viruses undergo changes in the antigenic properties of the virus particles due to the antigenic drift and shift observed in this virus. These changes have an impact on the physicochemical properties of the virus and in turn to the binding capacity of the virus to the chromatographic matrix. This could lead to high level of variation in the yields of the drifted or shifted strains making chromatography unsuitable for routine production. Another method used for the removal/reduction of host cell DNA.

Utilize higher concentration of benzonase (e.g. 50 U/ml, 100 U/ml), which is expensive.

The typical non-ionic surfactants used in pharmaceutical formulations include Triton™ X-100, Pluronic® F-68, F-88, and F-127 (poloxamers), Brij 35 (polyoxy-ethylene alkyl ether), polyoxyl stearate 40, Cremophor® EL, and alpha-tocopherol TPGS. Each of these surfactants have a common fact, in that they all contain polyoxyethylene moieties and thus to a greater or lesser extent, exhibit a similar problem, in that the polyoxyethylene moiety auto oxidizes to produce reactive peroxides, which causes an increase in unwanted protein immunogenicity. (Refer Edward T. Maggio et al; Polysorbates, peroxides, protein aggregation, immunogenicity—a growing concern; Journal of Excipients and Food Chemicals 3(2):46-53; 2012).

Various stabilizers are used to stabilize the vaccine preparation to achieve the desired shelf life. Stabilizers such as polyvinylpyrrolidone (PVP), trehalose and sorbitol are also used in virus formulations. However, PVP has been reported to destabilize live attenuated virus formulations. (Refer: J A White et al; Development of a stable liquid formulation of live attenuated influenza vaccine; Vaccine Volume 34, Issue 32, 12 Jul. 2016, Pages 3676-3683; 2016).

Trehalose is costly; it has to be combined with other sugars and protein additives (Gelatin) to achieve stability. Also, other stabilizers are better than trehalose for enhancing shelf life stability of a lyophilized vaccine.

Sorbitol has a low glass-transition temperature (Tg) (−1.6° C.), therefore cannot be used as a main formulation component. The low Tg of sorbitol limits its use. Sorbitol has to be combined with other sugars and protein additives (Gelatin) to achieve stability.

It has been suggested that the theoretical impact of host residual DNA on product safety should be considered for vaccine administration route, as the tissue distribution and rate of clearance could vary based on the administration modality. Studies demonstrate that the uptake and clearance of MDCK DNA from tissues vary depending on the route of administration. When DNA was administered intranasally, as compared to intramuscularly, detectable DNA levels were lower at all time points. Thus, the intranasal route of vaccine administration appears to reduce potential risk associated with residual host cell DNA that may be present in cell culture produced final vaccine products. (Refer: D. E. Tabor et al.; Biologicals 41 (2013) 247-253).

The present disclosure aims to overcome the aforementioned limitations and likewise provide compositions and methods for manufacturing an MDCK (Madin Darby canine kidney) cell based intranasally delivered live attenuated Influenza vaccine (LAIV) for protecting against influenza virus. The present disclosure further provides an improved manufacturing process that utilizes low concentration of endonuclease more particularly benzonase and is devoid of chromatography steps amenable to large scale cell culture production. Still further the present disclosure provides LAIV formulation devoid of polymers and surfactants, comprising one or more live attenuated influenza vaccine virus.

SUMMARY

The present disclosure provides a MDCK cell based intranasally delivered live attenuated Influenza vaccine (LAIV) composition comprising of:

a) One or more live attenuated Influenza vaccine virus;
   Wherein, the live attenuated Influenza vaccine virus strains are derived by "classical" or "reverse genetics" method of reassortment essentially consisting of the haemagluttinin (HA) gene and/or the neuraminidase (NA) gene from the wild type pandemic or seasonal influenza virus and the genes expressing the PB1, PB2, PA, NP, M and NS proteins and in some cases the NA protein derived from the master donor virus (MDV) the A/Leningrad/134/17/57 (H2N2) and/or B/USSR/60/69 strains,
b) One or more amino acid,
c) One or more carbohydrate, and
d) Gelatin.

The present disclosure further provides a method for manufacturing such vaccine composition/formulation.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide vaccine compositions and methods for manufacturing a live attenuated Influenza vaccine (LAIV) that can be delivered intranasally.

Yet another object of the present disclosure is to provide a Madin Darby canine kidney (MDCK) cell based live attenuated Influenza vaccine (LAIV) composition wherein the use of eggs is avoided altogether.

Yet another object of the present disclosure is to provide LAIV composition comprising one or more live attenuated influenza vaccine viruses and is devoid of polymers and surfactants.

Yet another object of the present disclosure is to provide LAIV composition comprising one or more live attenuated influenza vaccine viruses wherein the LAIV strains are based on cold adapted, temperature sensitive and attenuated phenotypes of master donor viruses (MDVs) containing one or two of the surface glycoprotein of the wild type pandemic or seasonal influenza strains.

Yet another object of the present disclosure is to provide MDCK cell based intranasally delivered live attenuated Influenza vaccine (LAIV) composition wherein, the composition preserves desired characteristics of a virus, including immunogenicity and stability.

Yet another object of the present disclosure is to provide a MDCK cell based intranasally delivered live attenuated Influenza vaccine (LAIV) composition/formulation suitable for treating or preventing Influenza virus infection, or to prevent, ameliorate, or delay the onset or progression of the clinical manifestations thereof.

Yet another object of the present disclosure is to provide an improved methodology in the field of MDCK cell based live attenuated Influenza vaccine production amenable for large scale cell culture production.

Other objects and advantages of the present disclosure will be more apparent from the following description, which is not intended to limit the scope of the present disclosure.

BRIEF DESCRIPTION OF THE DRAWING

The present disclosure will now be described with the help of the accompanying drawing enlisted below:

FIG. 6: Graph illustrates Stability at 37° C. of Influenza A Strain (A/17/California/2009/38—A/H1N1) & Influenza B Strain (B/Texas/02/13-CDC) Virus Log Yield Titers ($EID_{50}$/0.5 ml) with Stabilizer Composition 4 as disclosed in Table-3B FIG. 10: Graph illustrates Stability at 37° C. of Influenza A Strain (A/SouthAfrica/3626/13—H1N1) & Influenza B Strain (B/Texas/02/13-CDC) Virus Log Yield Titers ($EID_{50}$/0.5 ml) with Stabilizer Composition 1 as disclosed in Table-3B

FIG. 13: HI and VN antibody response post immunization. Geometric mean antibody responses at day 28 post final immunisation (study day 28 for one dose regime and study day 56 for two dose regime) against homologous challenge viruses H5/tk/Tk for H5 LAIV immunised animals and H7/An for H7 LAIV immunised animals. (a) HI antibody titres (b) VN antibody titers. N=6 per group, error bar represents the standard error of mean. Statistical significance was determined by Mann-Whitney's U test. *p<0.05 and **p<0.01.

DESCRIPTION

Figure 1:
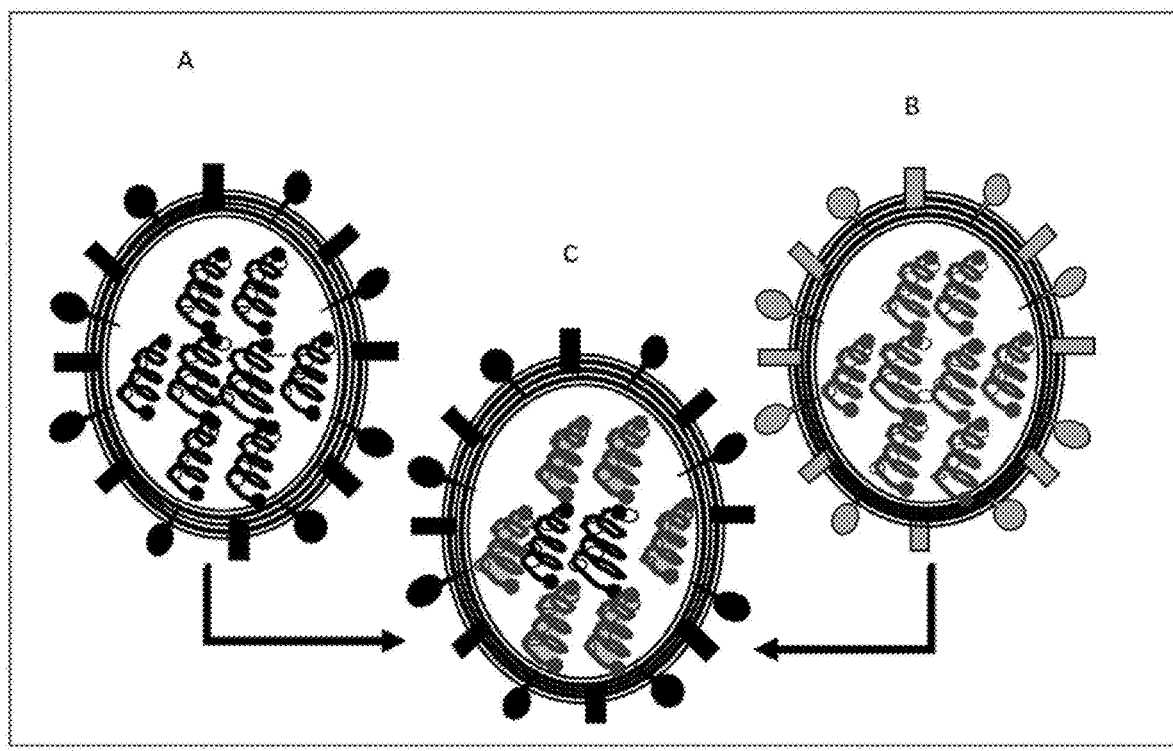
FIG. 1 illustrates a schematic representation of the reassortment of wild type pandemic or seasonal influenza virus and attenuated MDV generating the reassortant vaccine strain, Wherein (A) represents Wild type virus Infectious Pathogenic, (B) represents Master donor virus comprising Temperature sensitive (ts) Cold adapted (ca) and attenuated (at) phenotype gene segments and (C) represents Reassortant Vaccine strain.
Figure 2:
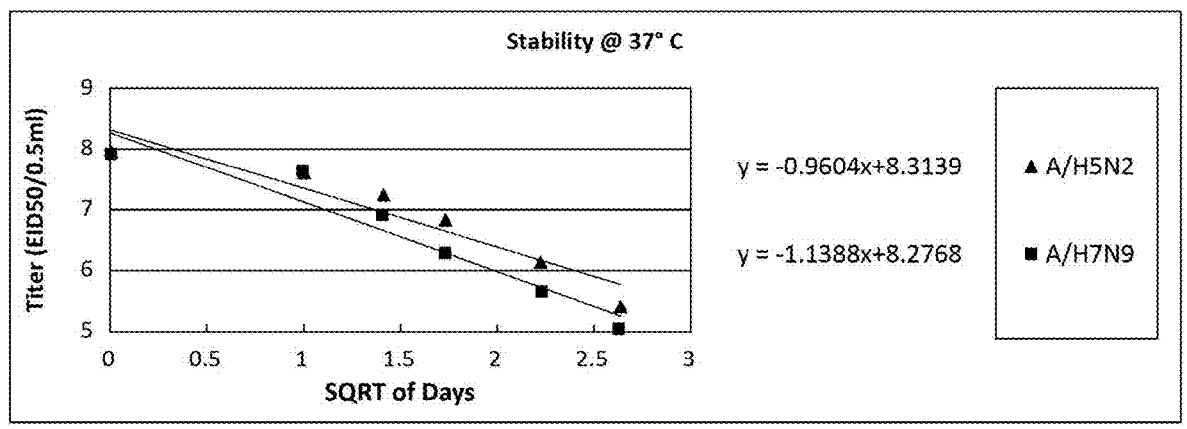
FIG. 2: Graph illustrates Stability at 37° C. of Influenza A Strain (A/17/turkey/Turkey/05/133—A/H5N2) Virus Log Yield Titers ($EID_{50}$/0.5 ml) with Stabilizer Composition 1 as disclosed in Table-3B
Figure 3:
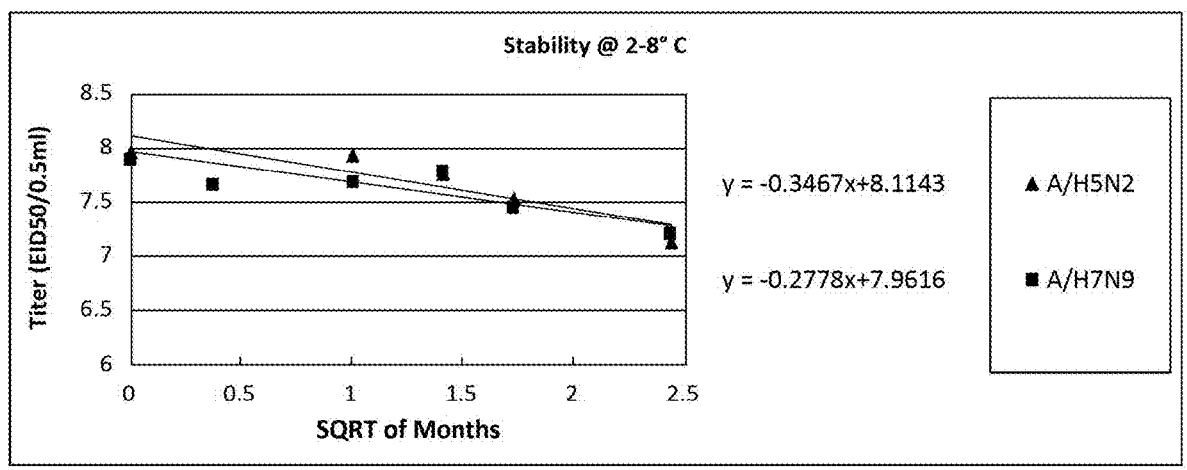
FIG. 3: Graph illustrates Stability at 2 to 8° C. of Influenza A Strain (A/17/turkey/Turkey/05/133—A/H5N2 & A/17/Anhui/2013/61—A/H7N9) Virus Log Yield Titers ($EID_{50}$/0.5 ml) with Stabilizer Composition 1 as disclosed in Table-3A

Although the present disclosure may be susceptible to different embodiments, certain embodiments are shown in the drawing and following detailed discussion, with the understanding that the present disclosure can be considered an exemplification of the principles of the disclosure and is not intended to limit the scope of disclosure to that which is illustrated and disclosed in this description.

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

As used herein, the term "influenza virus" refers to RNA virus comprising Influenza A, B, C and D virus representing family Orthomyxoviridae. An influenza virus can be a live wild-type pandemic or seasonal Influenza virus, a live attenuated influenza vaccine virus, an inactivated influenza virus, a chimeric influenza virus, or a recombinant influenza virus.

The present disclosure provides compositions comprising live attenuated Influenza vaccine (LAIV) virus for protection against infection by influenza virus. The present disclosure further provides methods for manufacturing compositions comprising one or more influenza vaccine virus.

According to a first embodiment of the present disclosure, the LAIV composition may comprise one or more live attenuated Influenza vaccine virus, one or more amino acid, one or more carbohydrate and gelatin.

The term "live" is used in its conventional meaning, a live virus is a virus which has not been inactivated, i.e. a virus capable of replicating on permissive cells. A live attenuated Influenza vaccine virus is a virus which does not induce the disease caused by the corresponding wild-type virus in animals or humans and which is capable of inducing a specific immune response.

According to a second embodiment of the present disclosure, the one or more live attenuated Influenza vaccine virus may be derived by "classical" or "reverse genetics" method of reassortment comprising gene segments from one or more influenza virus strains.

According to first aspect of second embodiment, the reassortant live attenuated influenza vaccine virus are reassortant LAIV virus comprising cold adapted, temperature sensitive and/or attenuated phenotype gene segments (PB1, PB2, PA, NP, M and/or NS proteins) of master donor viruses (MDVs) strain and haemagluttinin (HA) and/or neuraminidase (NA) gene segments of the wild type pandemic or seasonal influenza type A or B or C virus strains in a ratio of 1:7, 2:6, 3:5, 4:4, 5:3, 6:2 or 7:1.

Yet preferably the reassortant live attenuated influenza vaccine virus may include gene segments from the master donor virus (MDV) strain and the wild type pandemic or seasonal influenza virus strain in a ratio of 6:2 (As illustrated in FIG. 1).

According to a second aspect of second embodiment, the reassortant live attenuated influenza vaccine virus may include gene segments from the master donor virus (MDV) derived from Influenza A virus of any subtype or may be derived from Influenza B virus of any subtype.

The reassortant live attenuated influenza vaccine virus may include gene segments from the master donor virus (MDV) selected from the group comprising of A/Leningrad/134/17/57 (H2N2) Influenza A strain, B/USSR/60/69 Influenza B strain.

Yet preferably the reassortant live attenuated influenza type A vaccine virus may include gene segments from the master donor virus (MDV) comprising of A/Leningrad/134/17/57 (H2N2) Influenza A strain.

Yet preferably the reassortant live attenuated influenza vaccine type A virus strain—A/17/California/2009/38 may include gene segments from the master donor virus (MDV) comprising of A/Leningrad/134/17/57 (H2N2) Influenza A strain.

Yet preferably the reassortant live attenuated influenza vaccine type A virus strain—A/17/turkey/Turkey/05/133 may include gene segments from the master donor virus (MDV) comprising of A/Leningrad/134/17/57 (H2N2) Influenza A.

Yet preferably the reassortant live attenuated influenza vaccine type A virus strain—A/17/Anhui/2013/61 may include gene segments from the master donor virus (MDV) comprising of A/Leningrad/134/17/57 (H2N2) Influenza A.

Yet preferably the reassortant live attenuated influenza vaccine type A virus strain—A/17/New York/15/5364 may include gene segments from the master donor virus (MDV) comprising of A/Leningrad/134/17/57 (H2N2) Influenza A.

Yet preferably the reassortant live attenuated influenza vaccine type A virus strain—A/17/Hong-Kong/2014/8296 may include gene segments from the master donor virus (MDV) comprising of A/Leningrad/134/17/57 (H2N2) Influenza A.

Yet preferably the reassortant live attenuated influenza vaccine type A virus strain—A/South-Africa/3626/2013-CDC-LV14A may include gene segments from the master donor virus (MDV) comprising of A/Leningrad/134/17/57 (H2N2) Influenza A.

Yet preferably the reassortant live attenuated influenza type B vaccine virus may include gene segments from the master donor virus (MDV) comprising of B/USSR/60/69 Influenza B strain.

Yet preferably the reassortant live attenuated influenza vaccine type B virus strain—B/Texas/02/2013-CDC-LV8B may include gene segments from the master donor virus (MDV) comprising of B/USSR/60/69 Influenza B strain.

Yet preferably the reassortant live attenuated influenza vaccine type B virus strain—B/Phuket/3073/2013 may include gene segments from the master donor virus (MDV) comprising of B/USSR/60/69 Influenza B strain.

Yet preferably the reassortant live attenuated influenza vaccine type B virus strain—B/56/Brisbane/60/08 may include gene segments from the master donor virus (MDV) comprising of B/USSR/60/69 Influenza B strain.

According to third aspect of second embodiment, the reassortant live attenuated influenza vaccine virus may include the haemagluttinin (HA) gene and/or the neuraminidase (NA) gene from the Influenza A virus or Influenza B virus or Influenza C virus.

Yet preferably the reassortant live attenuated influenza A vaccine virus strain may include the haemagluttinin (HA) gene from influenza A virus HA subtypes H1, H2, H3, H4, H5, H6, H7, H8, H9, H10, H11, H12, H13, H14, H15, H16, H17 or H18 or any other reported HA subtype and/or neuraminidase (NA) gene from influenza A virus NA subtypes N1, N2, N3, N4, N5, N6, N7, N8, N9, N10 or N11 or any other reported NA subtype.

Yet preferably the reassortant live attenuated influenza vaccine virus may include the haemagluttinin (HA) gene and/or the neuraminidase (NA) gene from the pandemic influenza virus strains or potentially pandemic influenza virus strains.

Yet preferably the reassortant live attenuated influenza vaccine virus may include the haemagluttinin (HA) gene and/or the neuraminidase (NA) gene from the seasonal influenza virus strains.

Yet preferably the reassortant live attenuated influenza vaccine virus strain may contain the haemagluttinin (HA) gene and/or the neuraminidase (NA) gene from the influenza A virus subtypes H1N1, H2N2, H3N2, H5N1, H5N2, H9N2, H7N1, H7N3, H7N7, H6N1, H7N9, and H10N8 or any other previously reported or newly detected virus strain.

Yet preferably the reassortant live attenuated influenza vaccine virus strain may contain the haemagluttinin (HA) gene and/or the neuraminidase (NA) gene from the influenza A virus pdmH1N1 strain.

Yet preferably the reassortant live attenuated influenza vaccine virus strain may contain the haemagluttinin (HA) gene and/or the neuraminidase (NA) gene from the influenza A virus A/California/07/2009 (referred to as A/Cal)-like strain.

Yet preferably the reassortant live attenuated influenza vaccine virus strain may contain the haemagluttinin (HA) gene and/or the neuraminidase (NA) gene from the influenza A virus A/Michigan/45/2015-like strain.

Yet preferably the reassortant live attenuated influenza vaccine virus strain may contain the haemagluttinin (HA) gene and/or the neuraminidase (NA) gene from the influenza A virus strain—A/South-Africa/3626/2013 like strain.

Yet preferably the reassortant live attenuated influenza vaccine virus strain may contain the haemagluttinin (HA) gene and/or the neuraminidase (NA) gene from the influenza A virus H3N2-A/HongKong/4801/2014 like strain.

Yet preferably the reassortant live attenuated influenza vaccine virus strains may contain the haemagluttinin (HA) gene and/or the neuraminidase (NA) gene from the influenza B viruses belonging to two different lineages either Yamagata-like or Victoria-like.

Yet preferably the reassortant live attenuated influenza vaccine virus strains may contain the haemagluttinin (HA) gene and/or the neuraminidase (NA) gene from the influenza B virus Victoria lineage-B/Brisbane/60/2008-like strain.

Yet preferably the reassortant live attenuated influenza vaccine virus strains may contain the haemagluttinin (HA) gene and/or the neuraminidase (NA) gene from the influenza B virus Yamagata lineage-B/Phuket/3073/2013-like strain.

There are Two Methods for the Generation of Reassortants

1. Classical Method of Reassortment

The process of reassortment of wild type pandemic or seasonal influenza vaccine virus and attenuated MDV generating the reassortant strain includes co-infecting a culture host, usually eggs, with a MDV strain and a wild type virus strain. Reassortant viruses are selected by adding antibodies with specificity for the HA and/or NA proteins of the MDV in order to select for reassortant viruses that contain the wild type virus strain's HA and/or NA proteins. Over several passages of this treatment one can select for fast growing reassortant viruses containing the wild type pandemic or seasonal influenza vaccine virus strains HA and/or NA segments and the internal genes of the MDV.

2. Reverse Genetics Method of Reassortment

Reverse genetics is a method of generating infectious virus particles from DNA copies. The six internal genes of the MDV and the HA and NA gene from the wild type strain recommended for the inclusion in the vaccine are cloned in plasmids that can generate full length viral RNA when transfected in culture cells. These plasmids along with four plasmids expressing the viral polymerase subunit are transfected into culture cells. Expression of the polymerase subunit and generation of full-length viral RNA leads to virus assembly and release of infectious virus particles in the supernatant. This rescued virus exhibits the antigenic characteristics of the recommended strains and the ca, ts, att phenotype of the MDV.

The reassortant LAIV strain are procured from Institute of Experimental Medicine (IEM), St. Petersburg, Russia or WHO collaborating centres such as Centre for Disease Control and Prevention (CDC), Atlanta.

According to a third embodiment of the present disclosure, the LAIV composition may comprise one or more carbohydrates, selected from the group of but are not limited to, natural carbohydrates, synthetic carbohydrates, polyols, glass transition facilitating agents monosaccharides, disaccharides, trisaccharides, oligosaccharides and their corresponding sugar alcohols, polyhydroxyl compounds such as carbohydrate derivatives and chemically modified carbohydrates, hydroxyethyl starch and sugar copolymers. Both natural and synthetic carbohydrates are suitable for use. Synthetic carbohydrates include, but are not limited to, those which have the glycosidic bond replaced by a thiol or carbon bond. Both D and L forms of the carbohydrates may be used. The carbohydrate may be non-reducing or reducing. Where a reducing carbohydrate is used, the addition of inhibitors of the Maillard reaction is preferred. Reducing carbohydrates suitable for use in the composition are those known in the art and include, but are not limited to, glucose, sucrose, maltose, lactose, fructose, galactose, mannose, maltulose and lactulose. Non-reducing carbohydrates include, but are not limited to, non-reducing glycosides of polyhydroxyl compounds selected from sugar alcohols and other straight chain polyalcohols. Other useful carbohydrates include raffinose, stachyose, melezitose, dextran, cellobiose, mannobiose and sugar alcohols. The sugar alcohol glycosides are preferably monoglycosides, in particular the compounds obtained by reduction of disaccharides such as lactose, maltose, lactulose and maltulose. Glass forming agent is selected from the group consisting of sucrose, mannitol, trehalose, mannose, raffinose, lactitol, lactobionic acid, glucose, maltulose, isomaltulose, maltose, lactose sorbitol, dextrose, fructose, glycerol, or a combination thereof.

Yet according to the preferred aspect of the third embodiment, the LAIV composition may include sucrose as suitable carbohydrate stabilizer ranging in between 1% and 20% weight/volume, preferably in between 1-10%, more preferably in between 3-6%, most preferably equal to 4% (w/v).

According to fourth embodiment of the present disclosure, the LAIV composition may comprise one or more amino acid selected from the group of but is not limited to, Tricine, arginine, leucine, iso-leucine, histidine, glycine, glutamine, lysine, alanine, peptide, hydrolysed protein or protein such as serum albumin.

Yet according to the preferred aspect of the fourth embodiment, the LAIV composition may comprise of Tricine, arginine, histidine and alanine as suitable amino acids individually or in combination.

Yet according to the preferred aspect of the fourth embodiment, the one or more amino acid may include tricine ranging in between 0.1% and 2% weight/volume (w/v), preferably in between 0.1-1%, more preferably in between 0.1-0.5%, most preferably equal to 0.3% (w/v).

Yet according to the preferred aspect of the fourth embodiment, the one or more amino acid may include histidine ranging in between 0.1% to 2% (w/v), preferably in between 0.1-1%, more preferably in between 0.1-0.5%, most preferably equal to 0.21% (w/v).

Yet according to the preferred aspect of the fourth embodiment, the one or more amino acid may include alanine ranging in between 0.01% and 1% weight/volume, preferably in between 0.05-0.5%, more preferably in between 0.08-0.2%, most preferably equal to 0.1% (w/v).

Yet according to the preferred aspect of the fourth embodiment, the one or more amino acid may include arginine ranging in between 0.1% and 10% weight/volume, preferably in between 0.1-5%, more preferably in between 0.1-3%, most preferably equal to 2.1% (w/v).

According to fifth embodiment of the present disclosure, the LAIV composition may comprise gelatin ranging in between 0.1% and 10% weight/volume, preferably in between 0.1-5%, more preferably in between 0.1-3%, most preferably equal to 0.85% (w/v).

As used herein, the term "gelatin" means a sterile non-pyrogenic protein preparation (e.g., fractions) produced by partial acid hydrolysis (type A gelatin) or by partial alkaline hydrolysis (type B gelatin) of animal collagen, most commonly derived from cattle, pig, and fish sources. Gelatin can be obtained in varying molecular weight ranges. Recombinant sources of gelatin may also be used.

According to a sixth embodiment of the present disclosure, the LAIV composition may additionally comprise a buffering agent selected from the group consisting of HEPES, Citrate-phosphate, carbonate, phosphate, citrate, lactate, gluconate and tartrate buffering agents, as well as more complex organic buffering agents including a phosphate buffering agent that contains sodium phosphate and/or potassium phosphate in a ratio selected to achieve the desired pH. In another example, the buffering agent contains Tris (hydroxymethyl) aminomethane, or "Tris", formulated to achieve the desired pH. Yet in another example, the buffering agent could be the minimum essential medium with Hanks salts.

According to a seventh embodiment of the present disclosure, wherein the single dose composition is free of preservative and the multi-dose composition may additionally comprise preservative selected from the group comprising of 2-phenoxyethanol, Benzethonium chloride (Phemerol), Phenol, m-cresol, Thiomersal, Formaldehyde, paraben esters (e.g. methyl-, ethyl-, propyl- or butyl-paraben), benzalkonium chloride, benzyl alcohol, chlorobutanol, p-chlorm-cresol, or benzyl alcohol or a combination thereof. A vaccine composition may include material for a single immunization, or may include material for multiple immunizations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

According to an eighth embodiment of the present disclosure, the LAIV composition may additionally comprise pharmaceutically acceptable transporter, excipient, binder, carrier, isotonic agent, emulsifier or humectant wherein pharmaceutically acceptable excipients selected from the group consisting of surfactants, polymers and salts. Examples of Surfactants may include non-ionic surfactants such as polysorbate 20, polysorbate 80, etc. Examples of the polymers may include dextran, carboxymethylcellulose, hyaluronic acid, cyclodextrin, etc. Examples of the salts may include NaCl, KCl, $KH_2PO_4$, $Na_2HPO_4.2H_2O$, $CaCl_2$, $MgCl_2$, etc.

According to a ninth embodiment of the present disclosure, the LAIV composition may additionally comprise of an adjuvant selected from the group of aluminum hydroxide, aluminum phosphate, aluminum hydroxyphosphate, and potassium aluminum sulfate or a mixture thereof.

According to a tenth embodiment of the present disclosure, the LAIV composition may additionally comprise of an immunostimulatory component selected from the group consisting of an oil and water emulsion, MF-59, a liposome, a lipopolysaccharide, a saponin, lipid A, lipid A derivatives, Monophosphoryl lipid A, 3-deacylated monophosphoryl lipid A, AS01, AS03, an oligonucleotide, an oligonucleotide comprising at least one unmethylated CpG and/or a liposome, Freund's adjuvant, Freund's complete adjuvant, Freund's incomplete adjuvant, polymers, co-polymers such as polyoxyethylene-polyoxypropylene copolymers, including block co-polymers, polymer p 1005, CRL-8300 adjuvant, muramyl dipeptide, TLR-4 agonists, flagellin, flagellins derived from gram negative bacteria, TLR-5 agonists, fragments of flagellins capable of binding to TLR-5 receptors, Alpha-C-galactosylceramide, Chitosan, Interleukin-2, QS-21, ISCOMS, saponin combination with sterols and lipids.

According to an eleventh embodiment of the present disclosure, the method of preparing MDCK cell culture based LAIV composition may comprise any subset or all of the following steps:
  a) The LAIV candidate vaccine virus is initially passaged in SPF embryonated hen eggs producing egg based Master Seed Virus (MSV).
  b) Egg based Master Seed Virus is adapted to grow in Cell culture host to prepare cell based Working Seed Virus (WSV). This cell based WSV is sub cultured and propagated in host cells using different cell culture vessels/systems like Tissue Culture Flasks (TCFs) of surface area 175 $cm^2$, Roller Bottles (RBs) of surface area 850 $cm^2$, Cell Factories (CFs) of surface area 6320 $cm^2$ and fixed-bed Bioreactor (e.g., the iCELLis® Bioreactors from Pall® Life Sciences, Port Washington, N.Y., such as the Nano and 500/100 bioreactors).
  c) The Cultured Virus is harvested.
  d) The viral harvest is filtered by direct flow filtration (DFF) through at least one clarification filter to obtain clarified virus pools (CVPs).

e) The CVPs are treated with a non-specific endonuclease to degrade cellular DNA.
f) The treated endonuclease treated CVP is subjected to tangential flow filtration.
g) Stabilizing the TFF concentrate with a stabilizer composition comprising one or more carbohydrate, one or more amino-acid and gelatin to form a stabilized viral harvest.
h) Sterilizing the stabilized TFF concentrate by DFF through at least one sterilization grade filter to obtain a Sterilized clarified monovalent virus pool (CMVP).
i) The sterilized CMVPs are stored in polycarbonate bottles at −60° C. or below.
j) Sterilized formulations are filled in vials and stored at 2-8° C.

According to a first aspect of eleventh embodiment, the egg based LAIV virus candidate adapted to grow in cell culture host could be any eukaryotic cell. Yet preferably the cell culture host could be either mammalian or avian cells. Suitable mammalian cells include, but are not limited to, hamster, cattle, primate (including humans and monkeys) and dog cells. Various cell types include, but are not limited to, kidney cells, fibroblasts, retinal cells and lung cells. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the CLDK and MDCK cell lines.

Further suitable cells include, but are not limited to: CHO; 293T; BHK; MRC 5; PER.C6; FRhl.2; WI-38; etc. Suitable cells are widely available e.g. from the American Type Cell Culture (ATCC) collection, from the Coriell Cell Repositories, or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Yet preferably the cell culture host could be Madin Darby canine kidney (MDCK) cells, selected from but not limited to ATCC CCL-34, MDCK 33016 cell-line (DSM ACC 2219), MDCK (ATCC CCL34 MDCK(NBL2)), MDCK 33016 (DSM ACC 2219), DSM ACC3309, ATCC CRL-12042, ATCC PTA-7909, ATCC PTA-7910, ATCC PTA-6500, ATCC PTA-6501, ATCC PTA-6502, ATCC PTA-6503, 'MDCK-S', 'MDCK-SF101', 'MDCK-SF102', 'MDCK-SF103' and FERM BP-7449.

Yet preferably the cell culture host could be Madin Darby canine kidney (MDCK) cells ATCC CCL 34 (NBL2).

According to a second aspect of eleventh embodiment, the MDCK cells may be cultured in Minimum essential medium (MEM) comprising 10% fetal bovine serum (FBS). Culturing of cells may occur at 37° C.±1° C. The pH value of the medium during multiplication of cells before infection may be in the range of pH 6.8 and pH 7.6 and more preferably between a value of pH 7.0 and pH 7.4.

Yet the MDCK cells could be cultured in serum-free or protein-free media.

According to a third aspect of eleventh embodiment, before infection the MDCK cells may be washed with MEM and subsequently with MEM containing protease in the range of 5 to 25 U/ml.

The protease could be selected from, however is not limited to, trypsin, chymotrypsin, fungal protease, pepsin, papain, bromelain, and subtilisin.

Yet preferably the protease could be trypsin obtained from porcine origin or bovine origin or fungal origin or bacterial origin.

Yet preferably the protease could be a recombinant trypsin expressed in host cells of Yeast or Plant or Bacteria selected from but not limited to *Aspergillus* spp, *Streptomyces griseus*, Corn, *E. coli, Pichia pastoris*. Preferably said recombinant trypsin is selected from Biogenomics (*E. coli* as host), D.K. Bio Pharma Pvt. Ltd (*E. coli* as host), Richcore (*Pichia pastoris* as host) and Gibco (Fungi).

Yet the preferred trypsin concentration is 12.5 U/ml.

According to a fourth aspect of eleventh embodiment, before infection the working seed virus may be activated by diluting the virus with MEM containing protease in the range of 5 to 25 U/ml and incubating at temperature of 31° C. to 33° C. for 10 to 60 minutes.

The protease could be selected from, however is not limited to trypsin, chymotrypsin, fungal protease, pepsin, papain, bromelain, and subtilisin.

Yet preferably the protease could be trypsin obtained from porcine origin or bovine origin or fungal origin or bacterial origin.

Yet preferably the protease could be a recombinant trypsin expressed in host cells of Yeast or Plant or Bacteria selected from but not limited to *Aspergillus* spp, *Streptomyces griseus*, Corn, *E. coli, Pichia pastoris*. Preferably said recombinant trypsin is selected from Biogenomics (*E. coli* as host), D.K. Bio Pharma Pvt. Ltd (*E. coli* as host), Richcore (*Pichia pastoris* as host) and Gibco (Fungi).

Yet the preferred trypsin concentration is 12.5 U/ml.

Yet the preferred trypsin concentration is 2000 to 3000 units of trypsin per roller bottle.

According to a fifth aspect of eleventh embodiment, infection of MDCK cells with LAIV virus candidate may occur at a MDCK cell density of preferably about 40-60× $10^6$/TCF for TCF, 150-180×$10^6$/RB for RB, and 7000-10000×$10^6$/BR(4 m$^2$) for the Bioreactor (4 m$^2$).

According to a sixth aspect of eleventh embodiment, LAIV virus candidate may be grown onto MDCK cells in adherent culture or in suspension culture mode.

According to a seventh aspect of eleventh embodiment, infection of MDCK cells with egg based LAIV virus candidate may occur at a MOI between 1:100 to 1:10000.

According to an eighth aspect of eleventh embodiment, post infection the MDCK cells may be cultured in Minimum essential medium (MEM) containing trypsin in the range of 5 to 25 U/ml and temperature at 32° C.±1° C. The pH value of the medium post infection could be in the range of pH 6.8 and pH 7.6 and most preferably in the range of 7.2-7.6.

According to a ninth aspect of eleventh embodiment, post infection the cell supernatant may be harvested post incubation period of 40 to 70 hrs; more preferably could be 54±8 hrs.

Yet alternatively multiple harvesting may be carried out at an appropriate time interval for about 4-5 times before discarding the input material and processed separately to obtain clarified monovalent virus pools (CMVPs).

Upon harvesting a virus yield of at least 7.0-9.2 Log $EID_{50}$/0.5 ml may be achieved.

According to a tenth aspect of eleventh embodiment, the medium containing the virus may be clarified, typically through filters of decreasing pore sizes (e.g., 6μ, 5μ, 0.8μ, 0.65μ, 0.45μ, 0.2μ). Suitable commercially available filters and filtration devices are well known in the art and can be selected by those of skill. Exemplary filtration devices could be made of Polypropylene or Cellulose acetate or Polyethersulfone and the commercially available filters could be Millipak (Millipore), Kleenpak (Pall) and Sartobran™ (Sartorius) filtration devices.

According to an eleventh aspect of eleventh embodiment, the filtered harvest may be treated with a non-specific endonuclease most preferably Benzonase with concentration varying in between 0.5 Units/ml to 2 Units/ml, at temperature ranging in between 30-34° C., for 2 to 6 hours and subsequently at temperature of 2 to 8° C. for 5 to 15 hours.

Yet alternatively the filtered harvest may be treated with a non-specific endonuclease most preferably benzonase in presence of divalent cation selected from the group consisting of Ca2+, Mg2+, Mn2+, and Cu2+ in an amount of between 0.1 mM to 100 mM.

Yet alternatively the filtered harvest may be treated with a non-specific endonuclease most preferably benzonase in presence of divalent cation $Mg^{2+}$ salt at concentration of 1 to 3 mM.

According to a twelfth aspect of eleventh embodiment, the Benzonase treated harvest may be further subjected to tangential flow filtration (TFF) typically through filters with a molecular weight cut off (MWCO) ranging in between 100 KDa-500 KDa resulting in 2× to 10× concentration of viral harvest and further results in the removal of residual impurities.

Yet preferable the residual impurities may comprise of residual DNA, residual bovine serum albumin (BSA) and residual host cell protein.

According to a thirteenth aspect of the eleventh embodiment, the process described above may result in a purified and concentrated LAIV virus harvest comprising traces of residual cellular DNA (<10 ng/dose), residual BSA (<50 ng/dose) and residual cellular proteins. Furthermore, according to the process described above, the overall recovery of purified viruses could be at least 40%.

According to a fourteenth aspect of the eleventh embodiment, the concentrated monovalent virus stock (TFF concentrate) may be stabilized with a stabilizer composition to obtain the final LAIV composition comprising one or more carbohydrate, one or more amino-acid and gelatin.

Yet preferably the concentrated virus stock (TFF concentrate) may be stabilized with a stabilizer composition comprising sucrose, histidine, alanine, tricine, arginine and gelatin in any combination thereof.

Yet preferably the concentrated virus stock (TFF concentrate) may be stabilized with a stabilizer composition comprising sucrose at a concentration of 1 to 10% (w/v), histidine at a concentration of 0.1% to 2% (w/v), alanine at a concentration of 0.01% to 1% (w/v), tricine at a concentration of 0.1% to 1% (w/v), arginine at a concentration of 0.1 to 5% (w/v) and gelatin at a concentration of 0.1 to 5% (w/v).

Yet preferably the concentrated virus stock (TFF concentrate) may be stabilized with a stabilizer composition comprising sucrose at a concentration of 3 to 6% (w/v), histidine at a concentration of 0.1% to 1% (w/v), alanine at a concentration of 0.05% to 0.5% (w/v), tricine at a concentration of 0.1% to 0.5% (w/v), arginine at a concentration of 0.1 to 3% (w/v) and gelatin at a concentration of 0.1 to 3% (w/v).

Yet preferably the concentrated virus stock (TFF concentrate) may be stabilized with a stabilizer composition comprising sucrose 4% (w/v), histidine 0.21% (w/v), alanine 0.1% (w/v), tricine 0.3% (w/v), arginine 2.1% (w/v) and gelatin 0.85% (w/v).

According to a fifteenth aspect of the eleventh embodiment, the stabilized viral harvest may be sterilized by direct flow filtration (DFF) through at least one sterilization grade filters preferably 0.2µ. Suitable commercially available filters and filtration devices are well known in the art and can be selected by those of skill. Exemplary filtration devices could be made of Polypropylene or Cellulose acetate or Polyethersulfone or Polyvinylidene difluoride and the commercially available filters could be Millipak (Millipore), Kleenpak (Pall) and Sartobran™ P (Sartorius) filtration devices.

According to a sixteenth aspect of eleventh embodiment, the LAIV composition may be multivalent comprising more than one LAIV virus strain or subtype as disclosed in the earlier embodiments. The LAIV composition may be Bivalent or trivalent or tetravalent.

Yet alternatively the LAIV composition may be monovalent comprising any one of LAIV virus strain or subtype as disclosed in the earlier embodiments.

According to a seventeenth aspect of eleventh embodiment, the LAIV composition may comprise of Influenza virus at a dose of 6 to 7 Log $EID_{50}$ per 0.5 ml.

Yet preferably the LAIV composition may comprise of influenza type A virus or any subtype at a dose of 6 to 7 Log $EID_{50}$ per 0.5 ml; more preferably NLT 7 Log $EID_{50}$ per 0.5 ml.

Yet preferably the LAIV composition may comprise of Influenza type B virus or any subtype at a dose of 6 to 7 Log $EID_{50}$ per 0.5 ml; more preferably NLT 6.5 Log $EID_{50}$ per 0.5 ml.

According to a twelfth embodiment, method of preparing an immunogenic composition may comprise of following steps:
a) Infecting MDCK Cell culture host with Influenza virus at a MOI between 1:100 to 1:10000
b) Harvesting of Supernatant comprising Influenza virus post incubation period of 40 to 70 hrs in MEM containing trypsin in the range of 5 to 25 U/ml;
c) Filtering the viral harvest by direct flow filtration (DFF) through at least one clarification filter having a pore size of between about 6 micrometers to about 0.45 micrometers;
d) Treating the CVP with a non-specific endonuclease at temperature ranging in between 30-34° C. for 2 to 6 hours and subsequently at temperature of 2 to 8° C. for 5 to 15 hours;
e) Concentrating the endonuclease treated CVP by tangential flow filtration (TFF) using a membrane with a molecular weight cut off (MWCO) of 100 KDa-500 KDa;
f) Stabilizing the TFF concentrate with a stabilizer composition comprising one or more carbohydrate, one or more amino-acid and gelatin to form a stabilized viral harvest;
g) Sterilizing the stabilized TFF concentrate by DFF through at least one sterilization grade filter having a pore size of between about 0.8 micrometers to about 0.2 micrometers to form a sterilized CMVP;
wherein the overall recovery of purified viruses is more than or equal to 40%.

According to a first aspect of twelfth embodiment, the method of manufacturing the immunogenic composition wherein the step (d) may comprise of treating the viral harvest with non-specific endonuclease more particularly Benzonase having concentration in the range of 0.5 units/ml to 5 units/ml in presence of divalent cation selected from the group consisting of Ca2+, Mg2+, Mn2+, and Cu2+ in amount between 0.1 mM and 100 mM.

According to a second aspect of twelfth embodiment, the method of manufacturing the immunogenic composition wherein the step (d) may comprise of treating the viral harvest with non-specific endonuclease more particularly Benzonase having concentration in the range of 0.5 units/ml to 5 units/ml in presence of a divalent cation $Mg^{2+}$ salt at concentration of 1 to 3 mM.

According to a third aspect of twelfth embodiment, the method of manufacturing the immunogenic composition wherein the step (e) may comprise of concentrating the viral harvest by tangential flow filtration (TFF) resulting in at least 4× concentration of viral harvest.

According to a fourth aspect of twelfth embodiment, the method of manufacturing the immunogenic composition wherein the step (f) may comprise of stabilizing the viral harvest with a stabilizer composition comprising sucrose at a concentration of 1 to 10% (w/v), histidine at a concentration of 0.1% to 2% (w/v), alanine at a concentration of 0.01% to 1% (w/v), tricine at a concentration of 0.1% to 2% (w/v), arginine at a concentration of 0.1 to 5% (w/v) and gelatin at a concentration of 0.1 to 5% (w/v).

According to a fifth aspect of twelfth embodiment, the method of manufacturing the immunogenic composition, wherein the step (f) may comprise of stabilizing the viral harvest with a stabilizer composition comprising sucrose at a concentration of 3 to 6% (w/v), histidine at a concentration of 0.1% to 1% (w/v), alanine at a concentration of 0.05% to 0.5% (w/v), tricine at a concentration of 0.1% to 0.5% (w/v), arginine at a concentration of 0.1 to 3% (w/v) and gelatin at a concentration of 0.1 to 3% (w/v).

According to a sixth aspect of twelfth embodiment, the method of manufacturing the immunogenic composition, wherein the step (f) may comprise of stabilizing the viral harvest with a stabilizer composition comprising sucrose 4% (w/v), histidine 0.21% (w/v), alanine 0.1% (w/v), tricine 0.3% (w/v), arginine 2.1% (w/v) and gelatin 0.85% (w/v).

According to a sixth aspect of twelfth embodiment, the method of manufacturing the immunogenic composition, wherein the step (f) may comprise of stabilizing the viral harvest with a stabilizer composition comprising sucrose 4% (w/v), histidine 0.21% (w/v), alanine 0.1% (w/v), tricine 0.3% (w/v), arginine 2.1% (w/v) and gelatin 1.0% (w/v).

According to a seventh aspect of twelfth embodiment, the method of manufacturing the immunogenic composition, wherein the step (f) may comprise of stabilizing the viral harvest with a stabilizer composition comprising sucrose 4% (w/v), histidine 0.21% (w/v), alanine 0.1% (w/v), tricine 0.3% (w/v), arginine 1.6% (w/v) and gelatin 1.0% (w/v).

According to a thirteenth embodiment of the present disclosure, the immunogenic composition may comprise of a) One or more live attenuated Influenza vaccine (LAIV) virus at a dose of 6 to 7 Log $EID_{50}$ per 0.5 ml; b) Sucrose 1 to 10% (w/v); c) Histidine 0.1% to 2% (w/v); d) Alanine 0.01% to 1% (w/v); e) Tricine 0.1% to 2% (w/v); f) Arginine 0.1 to 5% (w/v); g) Gelatin 0.1 to 5% (w/v).

Yet preferably the immunogenic composition may comprise of a) One or more live attenuated Influenza vaccine (LAIV) virus at a dose of 6 to 7 Log $EID_{50}$ per 0.5 ml; b) Sucrose 3 to 6% (w/v); c) Histidine 0.1% to 1% (w/v); d) Alanine 0.05% to 0.5% (w/v); e) Tricine 0.1% to 0.5% (w/v); f) Arginine 0.1 to 3% (w/v); g) Gelatin 0.1 to 3% (w/v).

Yet preferably the immunogenic composition may comprise of a) One or more live attenuated Influenza vaccine (LAIV) virus at a dose of 6 to 7 Log $EID_{50}$ per 0.5 ml; b) Sucrose 4% (w/v); c) Histidine 0.21% (w/v); d) Alanine 0.1% (w/v); e) Tricine 0.3% (w/v); f) Arginine 2.1% (w/v); g) Gelatin 0.85% (w/v).

Yet preferably the immunogenic composition may comprise of a) One or more live attenuated Influenza vaccine (LAIV) virus NLT at a dose of 6 to 7 Log $EID_{50}$ per 0.5 ml; b) Sucrose 4% (w/v); c) Histidine 0.21% (w/v); d) Alanine 0.1% (w/v); e) Tricine 0.3% (w/v); f) Arginine 2.1% (w/v); g) Gelatin 1% (w/v).

Yet preferably the immunogenic composition may comprise of a) One or more live attenuated Influenza vaccine (LAIV) virus at a dose of 6 to 7 Log $EID_{50}$ per 0.5 ml; b) Sucrose 4% (w/v); c) Histidine 0.21% (w/v); d) Alanine 0.1% (w/v); e) Tricine 0.3% (w/v); f) Arginine 1.6% (w/v); g) Gelatin 1% (w/v).

According to a fourteenth embodiment of the present disclosure, the LAIV composition may be fully liquid.

Yet alternatively the LAIV composition could be lyophilized or freeze dried composition.

As used herein the terms "Freeze-drying" or "lyophilize" or "lyophilization" involves lyophilization and refers to the process by which a suspension is frozen, after which the water is removed by sublimation at low pressure. As used herein, the term "sublimation" refers to a change in the physical properties of a composition, wherein the composition changes directly from a solid state to a gaseous state without becoming a liquid.

According to a fifteenth embodiment of the present disclosure, the LAIV composition may be formulated for use in a method for reducing the onset of or preventing a health condition involving administration of an effective amount of the LAIV composition to a human subject via intranasal or other routes of immunization.

According to the preferred aspect of the embodiment, the LAIV composition may be administered to a human subject via intranasal route. In one embodiment, it is an intranasal dispensing device, such as a device in the form of an aerosol (intranasal spray) or a drop delivery system. Liquid nasal formulations can be delivered via Nasal Spray, Instillation and rhinyle catheter, Compressed air nebulizers, Squeezed bottle, Metered-dose pump sprays like multi dose metered dose spray pumps or single/duo dose spray pump, spray device attached to a syringe. Other dosage forms can be selected from Nasal powders (Insufflators, Dry powder inhaler), Nasal Gels, Nasal drops, Solutions, Suspensions, Cosolvent system, Microspheres, Nanoparticles, Microemulsions, Nasal insert.

The intranasal delivery devices can be selected from but not limited to Becton Dickinson (BD) Accuspray™ delivery device, Bi-Directional™ Optinose nasal device, MAD Intranasal Mucosal Atomization device by Teleflex, AeroLife™ and AeroVax™ (AerovectRx, Inc., Atlanta, GA), Jet injector—PharmaJet® Stratis® Needle-Free Injector, MUNJIs Multi-use-nozzle jet injectors: Aquapuncture device, Hypospray®, MadaJet®, GentleJet®, Disposable-syringe Jet Injectors: Medi-Jector®, J-Tip®, Injex®, Vitajet™, Lectra-Jet HS, LectraJet® M3, ZetaJet™, PharmaJet®, Aktiv-Dry PuffHaler™ and Nasal spray flu shot device.

According to a sixteenth embodiment of the present disclosure, the LAIV composition may be formulated for use in a method for reducing the onset of or preventing a health condition comprising Influenza A virus infection or its subtypes as disclosed in earlier embodiment of the disclosure, Influenza B virus infection or its subtypes as disclosed in earlier embodiment of the disclosure or Influenza C virus infection or its subtypes as disclosed in earlier embodiment of the disclosure.

According to a seventeenth embodiment of the present disclosure, the LAIV composition may be administered intranasally in a dose effective for protection. The vaccines are administered in a manner compatible with the dosage formulation, and in such amount as will be prophylactically effective. The immunogenic composition of the present disclosure can be administered as primary prophylactic agents in adults or children at the risk of infection. For example, the live attenuated Influenza vaccine composition as disclosed herein can be used in adults or children at risk of Influenza virus infection.

More preferably the LAIV composition may be administered intranasally in a dosage volume of about 0.1 to 0.5 ml.

According to a eighteenth embodiment of the present disclosure, the LAIV composition could be formulated as single dose vials or multidose vials or multidose kit or as pre-filled syringes or nasal sprays wherein the said LAIV composition may be given in a single dose schedule, or preferably a multiple dose schedule in which a primary course of vaccination is followed by 1-2 separate doses given at subsequent time intervals required to maintain and or reinforce the immune response, for example, at 1-4 months for a second dose, and if needed, a subsequent dose(s) after several months or years or annual vaccination. The dosage regimen will also, at least in part, be determined on the need of a booster dose required to confer protective immunity.

According to a nineteenth embodiment of the present disclosure, the final pH of the immunogenic composition may comprise of 6.5 to 8.

Other embodiments disclosed herein also encompasses vaccine kit comprising a first container containing a lyophilized (freeze-dried) immunogenic composition and a second container containing an aqueous solution optionally saline or WFI (water for injection) for the reconstitution of the lyophilized (freeze-dried) LAIV composition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps and can mean "includes," "including," the term is open-ended, allowing for the presence of more than that which is recited so long as basic or novel characteristics of that which is recited is not changed by the presence of more than that which is recited, but excludes prior art embodiments.

Throughout this specification the word, "immunogenic composition" covers any composition that elicits an immune response against the antigen or immunogen of interest expressed from vectors; for instance, after administration into a subject, elicits an immune response against the targeted immunogen or antigen of interest. The terms "vaccine composition" and "vaccine" covers any composition that induces a protective immune response against the antigen of interest, or which efficaciously protects against the antigen; for instance, after administration or injection into the subject, elicits a protective immune response against the targeted antigen or immunogen or provides efficacious protection against the antigen or immunogen expressed from vectors.

The use of the expression "one or more" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the composition of this invention, within the scope of the invention, may occur to those skilled in the art upon reviewing the disclosure herein. Such variations or modifications are well within the spirit of this disclosure.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

Similarly, the components used in purification, e.g., filters, columns, are not intended to be in any way limiting or exclusionary, and can be substituted for other components to achieve the same purpose at the discretion of the practitioner.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustration of the disclosure and not as a limitation.

Technical Advantages:
1. Presently nearly all of the influenza vaccines manufactured use eggs as host for preparation of virus pool. There are certain disadvantages of using eggs for the manufacture of LAIV that can be overcome using cell culture as substrates. The limitations of using egg as substrate are:
   Limited suppliers of vaccine quality eggs and specific pathogen free eggs
   Advance ordering with a minimum of 4 months is required before the eggs become available.
   Some of the candidate pandemic strain cause fatal infection in poultry resulting in non-availability of substrate (eggs) for vaccine manufacturing.
   Egg-based manufacturing requires specialized facility for egg incubation, harvesting etc in turn limiting the capacity for rapid up scaling.
2. Tissue culture based manufacturing have the advantage of a completely controlled system with ease of up scaling.
3. In case of pandemic, manufacturing of the vaccine on large scale can be easily achieved using pre-existing tissue culture manufacturing units of other viral vaccines.
4. Virus obtained in cell cultures has a higher similarity with the circulating strains, in contrast with the virus produced in eggs, which might have antigenic modifications.
5. Minimum components involved in the vaccine composition.
6. Devoid of preservatives, polymers and surfactants.
7. Purification process utilizes low concentration of endonuclease (benzonase).
8. Purification processes devoid of costly and cumbersome chromatography steps.
9. Improved method of manufacturing such stable composition/formulation that results in improved yield.

10. Intranasal delivery is the easiest route of immunization since it does not require high level of expertise, is amenable to multidose presentation,
11. Not reported to be associated with Guillain Barre Syndrome and provide better protection due to delivery at the site of infection.
12. The liquid presentation of a vaccine which is difficult to achieve helps overcome the issue of limited lyophilization capacity, need for supply of diluents for reconstitution and the added steps of re-constitution required before the delivery of the vaccine.
13. The MDV backbone used for the generation of LAIV reassortants has a well established safety profile and reported to render high levels of protection.

EXAMPLES

The following examples are included to demonstrate preferred embodiments of the invention. It should be appreciated by those of skill in the art that the compositions and techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The reassortant LAIV strain are procured from Institute of Experimental Medicine (IEM), St. Petersburg, Russia or WHO collaborating centres such as Centre for Disease Control and Prevention (CDC), Atlanta.

Examples 1: Reassortant LAIV Virus Immunogenic Composition Stability Data

Component 1—Live Attenuated Influenza Vaccine Virus (LAIV)

The Influenza vaccine virus are reassortant LAIV virus derived by classical method of reassortment comprising cold adapted, temperature sensitive and/or attenuated phenotype gene segments of master donor viruses (MDVs) and haemagluttinin (HA) and/or neuraminidase (NA) gene segments of the wild type pandemic or seasonal influenza type A or B or C virus strains in a ratio of 6:2 or 7:1.

TABLE 1

Reassortant LAIV Virus Strain used in Immunogenic Composition

| Sr. No. | Influenza Subtype | Reassortant LAIV Strain | MDV |
|---|---|---|---|
| 1 | Type A-H5N2 | A/17/turkey/Turkey/05/133 | A/Leningrad/134/17/57 (H2N2) |
| 2 | Type A-H7N9 | A/17/Anhui/2013/61 | A/Leningrad/134/17/57 (H2N2) |
| 3 | Type A-H1N1 | A/17/California/2009/38 | A/Leningrad/134/17/57 (H2N2) |
| 4 | Type A-H1N1 | A/17/New York/15/5364 | A/Leningrad/134/17/57 (H2N2) |
| 5 | Type A-H1N1 | A/South-Africa/3626/2013-CDC- LV14A | A/Leningrad/134/17/57 (H2N2) |
| 6 | Type A-H3N2 | A/17/Hong-Kong/2014/8296 | A/Leningrad/134/17/57 (H2N2) |
| 7 | Type B Victoria lineage | B/Texas/02/2013-CDC- LV8B | B/USSR/60/69 |
| 8 | Type B Yamagata | B/Phuket/3073/2013 | B/USSR/60/69 |
| 9 | Type B Victoria lineage | B/56/Brisbane/60/08 | B/USSR/60/69 |

For LAIV Immunogenic composition:

Type A virus in the range of 6 to 7 log EID50/dose of 0.5 ml; more preferably 7 log EID50/dose of 0.5 ml Type B virus in the range of 6 to 7 log EID50/dose of 0.5 ml; more preferably 6.5 log EID50/dose of 0.5 ml The LAIV composition is either monovalent or Multivalent (bivalent; trivalent; quadrivalent) in terms of Reassortant LAIV Virus Strain used in Immunogenic Composition as disclosed in Table 1 in any combination thereof.

TABLE 2A

Stabilizer Composition in accordance with the present disclosure

| | Formulation | [w/v % per 0.5 ml Dose] | | | |
|---|---|---|---|---|---|
| No | Components | 1 | 2 | 3 | 4 |
| 1 | Gelatin | 0.85 | 0.85 | 1.0 | 1.0 |
| 2 | Sucrose | 4.0 | — | — | — |
| 3 | L-Histidine | 0.21 | 0.21 | 0.21 | 0.21 |
| 4 | L-Alanine | 0.1 | 0.1 | 0.1 | 0.1 |
| 5 | Tricine | 0.3 | 0.3 | 0.3 | 0.9 |
| 6 | L-Arginine Hydrochloride | 2.1 | 2.1 | 1.6 | 1.6 |
| 8 | Sorbitol | — | 5.0 | 5.0 | 5.0 |
| 9 | SAF | — | — | | |

TABLE 2B

Excipient Composition in accordance with the present disclosure

| Sr. No. | Excipient | % w/v per 0.5 ml Dose |
|---|---|---|
| 1 | Sodium Chloride | 0.8 |
| 2 | Potassium Chloride | 0.02 |
| 3 | Potassium Dihydrate Phosphate | 0.02 |
| 4 | Disodium Hydrogen Phosphate Dihydrate | 0.14 |

TABLE 3A

Real time Stability data at 2-8° C. for 6 Months (M)

| Sr. No. | Strain | Log EID$_{50}$/0.5 ml | | | | | Rate of degradation |
|---|---|---|---|---|---|---|---|
| | | 0 Day | 1 M | 2 M | 3 M | 6 M | |
| | Stabilizer Composition 3 | | | | | | |
| 1 | A/17/California/2009/38 (H1N1) | 7.92 | 8.245 | 7.89 | 7.69 | 6.72 | −0.47 |
| 2 | B/Texas/02/13-CDC (Type B) | 7.39 | 6.82 | 6.99 | 6.92 | 5.93 | −0.51 |
| | Stabilizer Composition 4 | | | | | | |
| 1 | A/17/California/2009/38 (H1N1) | 8.2 | 7.99 | 7.87 | 7.89 | 6.95 | −0.45 |
| 2 | B/Texas/02/13-CDC (Type B) | 7.25 | 6.75 | 6.65 | 6.92 | 5.93 | −0.46 |
| | Stabilizer Composition 2 | | | | | | |
| 1 | A/SouthAfrica/3626/13 (H1N1) | 7.88 | 7.82 | 7.65 | 7.06 | 7 | −0.4 |
| 2 | B/Texas/02/13-CDC (Type B) | 8.2 | 7.04 | 6.72 | 6.78 | 6.39 | −0.73 |
| | Stabilizer Composition 1 | | | | | | |
| 1 | A/SouthAfrica/3626/13 (H1N1) | 7.96 | 7.86 | 7.75 | 7.56 | 7.3 | −0.27 |
| 2 | B/Texas/02/13-CDC-LV8B (Type | 7.56 | 7.21 | 7.15 | 7.14 | 6.87 | −0.26 |
| 3 | A/17/turkey/Turkey/05/133(H5N2) | 7.96 | 7.93 | 7.76 | 7.52 | 7.12 | −0.34 |
| 4 | A/17/Anhui/2013/61(H7N9) | 7.89 | 7.68 | 7.78 | 7.43 | 7.2 | −0.27 |

TABLE 3B

Stress Stability data at 37° C. for 7 days (D)

| Sr. No. | Strain | Log EID$_{50}$/0.5 ml | | | | | | Rate of degradation |
|---|---|---|---|---|---|---|---|---|
| | | 0 Day | 1 D | 2 D | 3 D | 5 D | 7 D | |
| | Stabilizer Composition 3 | | | | | | | |
| 1 | A/17/California/2009/38 (H1N1) | 7.92 | 7.79 | 7.48 | 7.03 | 6.39 | 4.76 | −1.095 |
| 2 | B/Texas/02/13-CDC (Type B) | 7.39 | 6.96 | 6.76 | 6.64 | 5.47 | 4.88 | −0.952 |
| | Stabilizer Composition 4 | | | | | | | |
| 1 | A/17/California/2009/38 (H1N1) | 8.2 | 7.76 | 7.33 | 7.35 | 6.56 | 5.39 | −0.98 |
| 2 | B/Texas/02/13-CDC (Type B) | 7.25 | 6.99 | 6.93 | 6.49 | 5.85 | 4.92 | −0.84 |
| | Stabilizer Composition 2 | | | | | | | |
| 1 | A/SouthAfrica/3626/13 (H1N1) | 8.03 | 7.77 | 7.26 | 6.8 | 6.2 | 4.44 | −1.25 |
| 2 | B/Texas/02/13-CDC (Type B) | 8.25 | 7.18 | 6.05 | 5.43 | 5.06 | 3.98 | −1.62 |
| | Stabilizer Composition 1 | | | | | | | |
| 1 | A/SouthAfrica/3626/13 (H1N1) | 8.31 | 7.82 | 7.06 | 7.16 | 6.73 | 6.02 | −0.83 |
| 2 | B/Texas/02/13-CDC (Type B) | 7.03 | 6.98 | 6.56 | 6.18 | 5.72 | 5.05 | −0.76 |
| 3 | A/17/turkey/Turkey/05/133(H5N2) | 7.96 | 7.62 | 7.24 | 6.83 | 6.15 | 5.43 | −0.96 |

Figure 4:
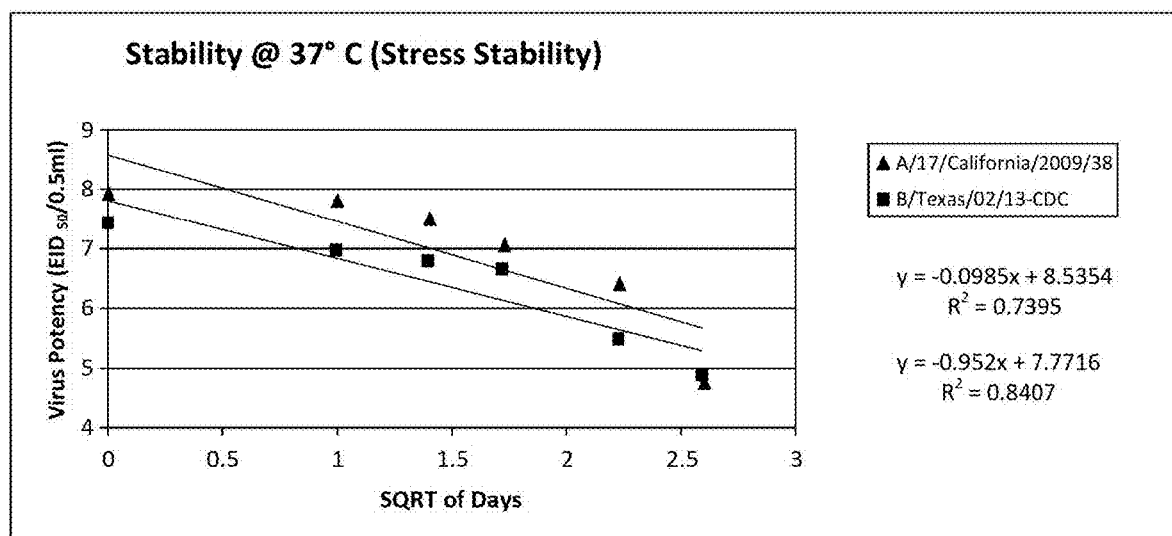
FIG. 4: Graph illustrates Stability at 37° C. of Influenza A Strain (A/17/California/2009/38-A/H1N1) & Influenza B Strain (B/Texas/02/13-CDC) Virus Log Yield Titers ($EID_{50}$/0.5 ml) with Stabilizer Composition 3 as disclosed in Table-3B
Figure 5:
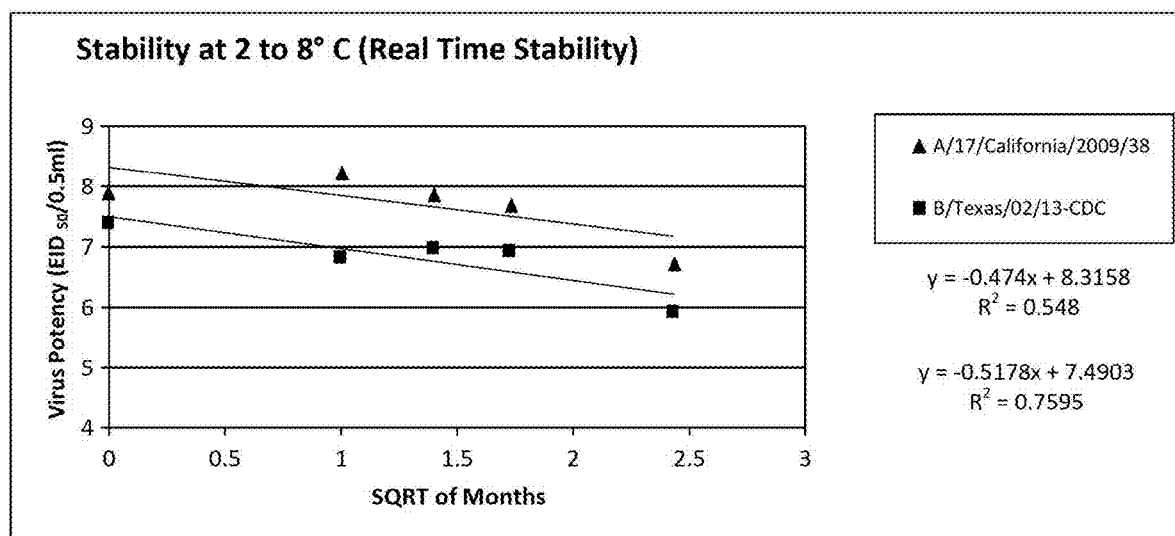
FIG. 5: Graph illustrates Stability at 2 to 8° C. of Influenza A Strain (A/17/California/2009/38—A/H1N1) & Influenza B Strain (B/Texas/02/13-CDC) Virus Log Yield Titers ($EID_{50}$/0.5 ml) with Stabilizer Composition 3 as disclosed in Table-3A

Interpretation:

Stabilizer Composition 3 (1% w/v Gelatin+5% w/v Sorbitol+0.1% w/v L-Alanine+0.21% w/v L-Histidine+0.3% w/v Tricine+1.6% w/v L-Arginine Hydrochloride):

Unacceptable rate of degradation was observed for both stress stability at 37° C. and real time stability at 2 to 8° C. temperatures for Type A/H1N1 and Type B influenza vaccine strains. (Refer FIGS. 4 & 5)

Figure 7:
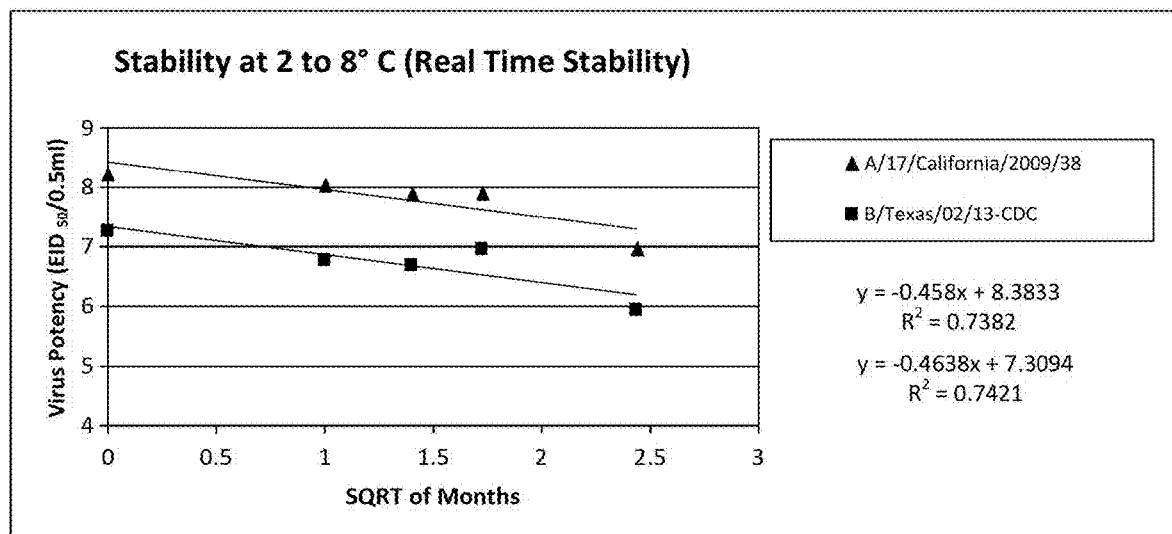
FIG. 7: Graph illustrates Stability at 2 to 8° C. of Influenza A Strain (A/17/California/2009/38—A/H1N1) & Influenza B Strain (B/Texas/02/13-CDC) Virus Log Yield Titers ($EID_{50}$/0.5 ml) with Stabilizer Composition 4 as disclosed in Table-3A

Stabilizer Composition 4 (1% w/v Gelatin+5% w/v Sorbitol+0.1% w/v L-Alanine+0.21% w/v L-Histidine+0.9% w/v Tricine+1.6% w/v L-Arginine Hydrochloride):

Unacceptable rate of degradation was observed for both stress stability at 37° C. and real time stability at 2 to 8° C. temperatures for Type A/H1N1 and Type B influenza vaccine strains. (Refer FIGS. 6 & 7)

Figure 8:
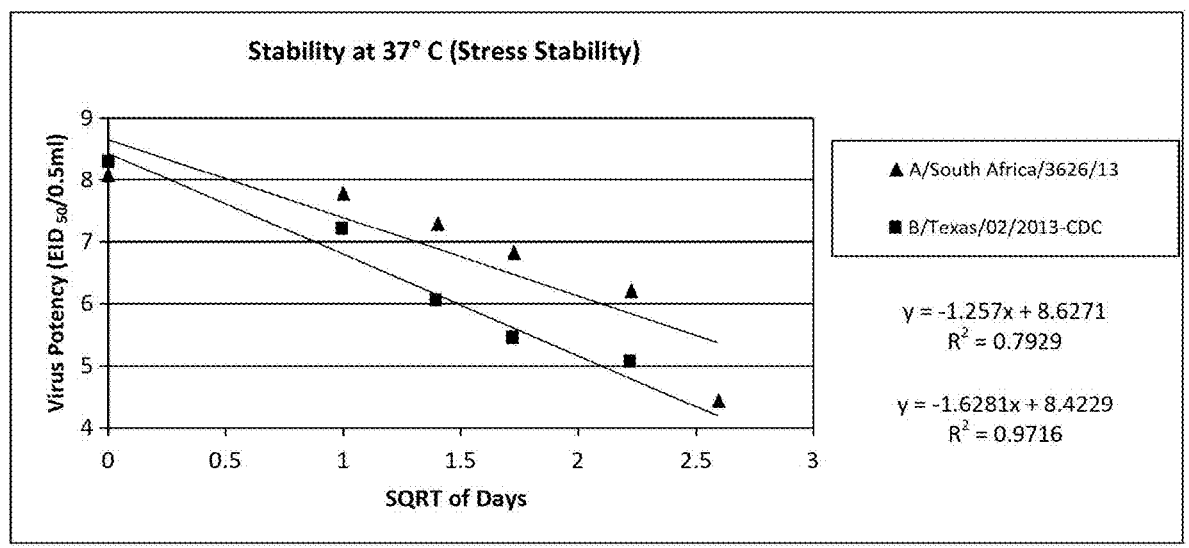
FIG. 8: Graph illustrates Stability at 37° C. of Influenza A Strain (A/SouthAfrica/3626/13—H1N1) & Influenza B Strain (B/Texas/02/13-CDC) Virus Log Yield Titers ($EID_{50}$/0.5 ml) with Stabilizer Composition 2 as disclosed in Table-3B
Figure 9:
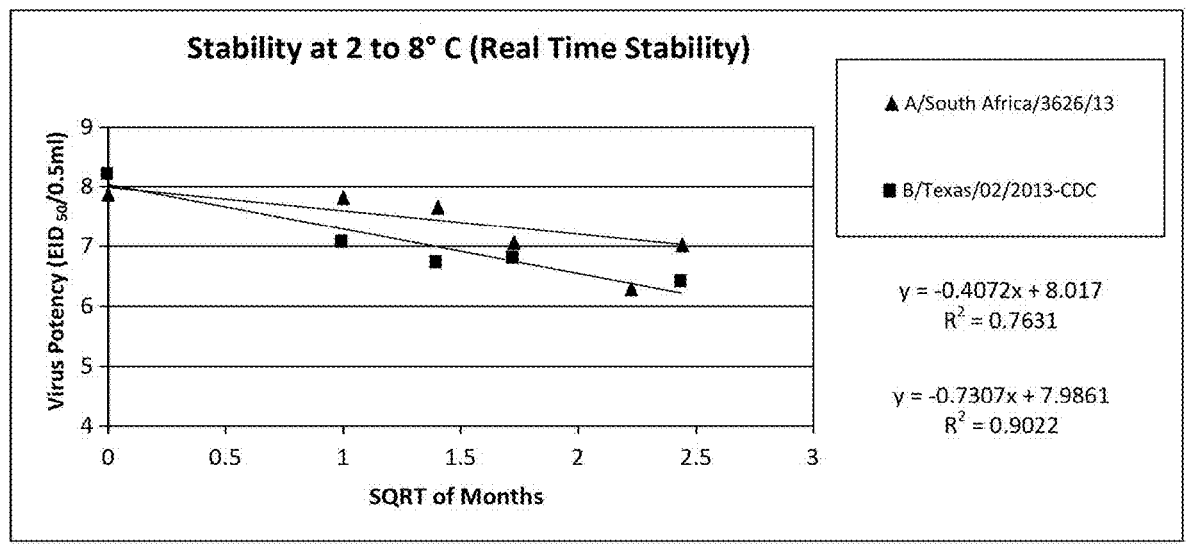
FIG. 9: Graph illustrates Stability at 2 to 8° C. of Influenza A Strain (A/SouthAfrica/3626/13—H1N1) & Influenza B Strain (B/Texas/02/13-CDC) Virus Log Yield Titers ($EID_{50}$/0.5 ml) with Stabilizer Composition 2 as disclosed in Table-3A
Figure 11:
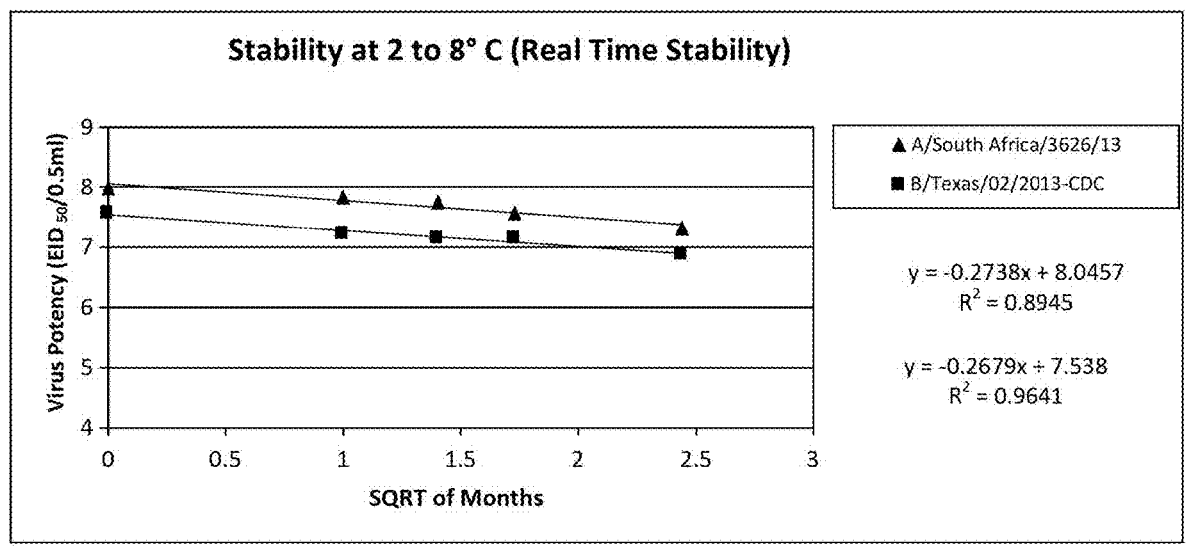
FIG. 11: Graph illustrates Stability at 2 to 8° C. of Influenza A Strain (A/SouthAfrica/3626/13—H1N1) & Influenza B Strain (B/Texas/02/13-CDC) Virus Log Yield Titers ($EID_{50}$/0.5 ml) with Stabilizer Composition 1 as disclosed in Table-3A

Stabilizer Composition 2 (0.85% w/v Gelatin+3% w/v Sucrose+0.1% w/v L-Alanine+0.21% w/v L-Histidine+ 0.3% w/v Tricine+2.1% w/v L-Arginine Hydrochloride):

Unacceptable rate of degradation was observed for both stress stability at 37° C. and real time stability at 2 to 8° C. temperatures. (Refer FIGS. 8 & 9)

Stabilizer Composition 1 (0.85% w/v Gelatin+4% w/v Sucrose+0.1% w/v L-Alanine+0.21% w/v L-Histidine+ 0.3% w/v Tricine+2.1% w/v L-Arginine Hydrochloride):

Acceptable rate of degradation (values are within acceptable range) was observed for both stress stability at 37° C. and real time stability at 2 to 8° C. temperatures. (Refer FIGS. 2, 3, 10 & 11)

Examples 2: MDCK Cell Based LAIV Virus Manufacturing Process

The process for preparing MDCK cell culture based LAIV composition may comprise any subset or all of the following steps:

k) The LAIV candidate vaccine virus is initially passaged in SPF embryonated hen eggs producing egg based Master Seed Virus (MSV).

l) Egg based Master Seed Virus is adapted to grow in MDCK Cell culture (ATCC CCL-34) host to prepare cell based Working Seed Virus (WSV). This Cell based WSV is used to infect MDCK Cell culture at a MOI between 1:100 to 1:10000 in different cell culture vessels/systems like Tissue Culture Flasks (TCFs) of surface area 175 cm$^2$, Roller Bottles (RBs) of surface area 850 cm$^2$, Cell Factories (CFs) of surface area 6320 cm$^2$ and fixed-bed Bioreactor (e.g., the iCELLis® Bioreactors from Pall® Life Sciences, Port Washington, N.Y., such as the Nano and 500/100 bioreactors). (MDCK cells were grown using MEM containing FBS; washed with MEM containing trypsin 5 to 25 U/ml prior to inoculation; WSV inoculated into cells at MOI between 1:10 to 1:10000 and incubated at 31-33° C. for 48-72 hours)

m) The Cultured Virus is harvested.

n) The viral harvest is filtered by direct flow filtration (DFF) through at least one clarification filter to obtain clarified virus pools (CVPs).

o) Treating the CVP with a non-specific endonuclease (for e.g. Benzonase) at temperature ranging in between 30-34° C. for 2 to 6 hours and subsequently at temperature of 2 to 8° C. for 5 to 15 hours;

p) Concentrating the endonuclease treated CVP by tangential flow filtration (TFF) using a membrane with a molecular weight cut off (MWCO) of 100 KDa-500 KDa;

q) Stabilizing the TFF concentrate with a stabilizer composition comprising one or more carbohydrate, one or more amino-acid and gelatin to form a stabilized viral harvest.

r) Sterilizing the stabilized TFF concentrate by DFF through at least one sterilization grade filter having a pore size of about 0.2 micrometers to form a to obtain a Sterilized CMVP (Clarified Monovalent Virus Pool).

s) The sterilized CMVPs are stored in polycarbonate bottles at −60° C. or below.

t) Sterilized formulations are filled in vials and stored at 2-8° C.

TABLE 4

MDCK Cell growth parameters

| Roller bottle system | | iCELLis Bioreactor system | |
|---|---|---|---|
| Seeding cell density | 15 × 10$^6$/RB | Seeding cell density | 1000 × 10$^6$ |
| Confluent cell density | 150 × 10$^6$/RB | Confluent cell density | 8000 × 10$^6$ |
| pH | 7.2 ± 0.2 | pH | 7.2 ± 0.2 |
| DO | NA | DO | 75% |
| Temperature | 37° C. ± 1° C. | Temperature | 37° C. ± 1° C. |
| Incubation duration | 3-5 days | Incubation duration | 3-5 days |

TABLE 5

Reassortant LAIV Virus growth parameters

| Roller bottle system | | iCELLis Bioreactor system | |
|---|---|---|---|
| MOI | 1:100 to 1:10000 | MOI | 1:100 to 1:10000 |
| Cell density at the time of infection | 150 × 10$^6$/RB | Cell density at the time of infection | 8000 × 10$^6$ |
| pH | 7.4 ± 0.2 | pH | 7.4 ± 0.2 |
| DO | NA | DO | 50% |
| Temperature | 32° C. ± 1° C. | Temperature | 32° C. ± 1° C. |
| Incubation duration/ Harvest period | Single harvest at 54 ± 6 hrs | Incubation duration/ Harvest period | Single harvest at 54 ± 6 hrs |

Cell Culture Medium: MEM with 10% FBS (pH adjusted with 1N HCl to 7.0 to 7.4)

(Additional Glutamine 350 mg/L)

Virus medium: MEM without FBS (pH adjusted with 1N HCl to 7.2 to 7.6)

(Additional Glucose—500 mg/L, Glutamine—350 mg/L)

Additional 0.4% of glucose is added in CM and VM used for bioreactor system

TABLE 6

MEM (Minimum Essential Medium)

| Sr. No. | COMPONENTS | MEM HANK'S (mg/L) |
|---|---|---|
| 1 | L_Arginine Hydrochloride | 126 |
| 2 | L-Cysteine 2HCL | 31 |
| 3 | L-Glutamine | 292 |
| 4 | L-Histidine HCl•H$_2$O | 42 |
| 5 | L-Isoleucine | 52 |
| 6 | L-Leucine | 52 |
| 7 | L-Lysine hydrochloride | 73 |
| 8 | L-Methionine | 15 |
| 9 | L-Phenylalanine | 32 |
| 10 | L-Threonine | 48 |
| 11 | L-Tryptophan | 10 |
| 12 | L-Valine | 46 |
| 13 | L-Tyrosine. Disodium salt | 52 |
| 14 | Calcium Chloride | 140 |
| 15 | Magnesium sulphate | 98 |
| 16 | Potassium Chloride | 400 |
| 17 | Sodium Chloride | 8000 |
| 18 | Potassium Phosphate Monobasic (anhydrous) | 60 |
| 19 | Sodium Phosphate Di basic | 48 |
| 20 | Choline Chloride | 1 |
| 21 | D-Calcium pantothenate | 1 |
| 22 | Folic acid | 1 |
| 23 | I-Inositol | 2 |
| 24 | Niacinamide | 1 |
| 25 | Pyridoxal HCl | 1 |
| 26 | Riboflavin | 0.1 |
| 27 | Thiamine HCl | 1 |
| 28 | D-Glucose | 1000 |
| 29 | Phenol red | 10 |
| 30 | NaHCO$_3$ 1.3 gm/lit for medium with FBS | |
| 31 | NaHCO$_3$ 0.75 gm/lit for medium without FBS | |

TABLE 7

Phosphate Buffered Saline (PBS) Preparation

| Component | Quantity per 1 L | Concentration (%) |
|---|---|---|
| Sodium Chloride | 8 g | 0.8 |
| Potassium Chloride | 0.2 g | 0.02 |
| Potassium Dihydrate Phosphate | 0.2 g | 0.02 |
| DiSodium Hydrogen Phosphate Dihydrate | 1.4 g | 0.14 |

TABLE 8

Stabilizer-I for MDCK cell based LAIV

| Component | Quantity per 1 L | Concentration (%) |
|---|---|---|
| Gelatin | 42.5 g | 4.25 |
| Sucrose | 200 g | 20 |

TABLE 9

Stabilizer-II for MDCK cell based LAIV

| Component | Quantity per 1 L | Concentration (%) |
|---|---|---|
| L-Histidine | 23.1 g | 2.31 |
| L-Alanine | 11.0 g | 1.1 |
| Tricine | 33.0 g | 3.3 |
| L-Arginine | 231 g | 23.1 |
| Gelatin | 8.5 g | 0.85 |
| Sucrose | 40 g | 4.0 |

TABLE 10

Blind Vaccine composition

| Component | Quantity per 1.1 L |
|---|---|
| PBS | 0.8 L |
| Stabilizer I for MDCK cell culture based liquid LAIV | 0.2 L |
| Stabilizer II for MDCK cell culture based liquid LAIV | 0.1 L |

Examples 3: Effect of Virus Input (MOI) and Post Inoculation Incubation Period on Yield

TABLE 11

Effect of Virus input (MOI) and post inoculation incubation period on Yield

| MOI used | 1:100 | 1:1000 | 1:10000 | 1:100 | 1:1000 | 1:10000 | 1:100 | 1:1000 | 1:10000 |
|---|---|---|---|---|---|---|---|---|---|
| Type A (H1N1) - A/17/California/2009/38 | | | | | | | | | |
| Incubation Period (Hrs) | 50 ± 2 | 50 ± 2 | 50 ± 2 | 60 ± 2 | 60 ± 2 | 60 ± 2 | 70 ± 2 | 70 ± 2 | 70 ± 2 |
| Titre ($EID_{50}$/0.5 ml) | 8.43 | 8.21 | 5.48 | 8.35 | 8.44 | 7.27 | 8.40 | 7.95 | 7.89 |
| Type A (H3N2) - A/17/Hong Kong/2014/8296 | | | | | | | | | |
| Incubation Period (Hrs) | 50 ± 2 | 50 ± 2 | 50 ± 2 | 60 ± 2 | 60 ± 2 | 60 ± 2 | 70 ± 2 | 70 ± 2 | 70 ± 2 |
| Titre ($EID_{50}$/0.5 ml) | 8.43 | 7.93 | 7.36 | 8.83 | 8.31 | 8.30 | 8.17 | 8.27 | 8.65 |
| Type B - B/Texas/02/2013-CDC-LV8B | | | | | | | | | |
| Incubation Period (Hrs) | 50 ± 2 | 50 ± 2 | 50 ± 2 | 60 ± 2 | 60 ± 2 | 60 ± 2 | 70 ± 2 | 70 ± 2 | 70 ± 2 |
| Titre ($EID_{50}$/0.5 ml) | 7.69 | 8.03 | 7.92 | 8.01 | 8.15 | 8.15 | 7.72 | 8.14 | 8.10 |

Inference:

A. Time of Infection:

On the basis of optimization studies specific limit of cell count of 120 to 180 million cells per roller bottle and 7000 to 10000 million cells for bioreactor system was selected for the infection of MDCK cell derived influenza working seed virus. Microscopic observation of roller bottles with MDCK cells were done for monolayer confluency before infection procedure.

B. MOI and Post Inoculation Incubation Period:

On the basis of all observations of MOI optimization studies the range of MOI selected for Type A (H1N1), Type A (H3N2) and Type B influenza viruses was between 1:100 to 1:10000 and the range of post inoculation incubation period was between 48 hrs to 72 hrs.

Examples 4: Effect of Different Concentrations of Trypsin on Yield

TABLE 12

Different concentrations of trypsin

| Sr. No. | Trypsin units/Roller bottle | $EID_{50}$/0.5 ml |
|---|---|---|
| 1 | 5000 | 8.6 |
| 2 | 4000 | 8.72 |
| 3 | 3000 | 8.85 |
| 4 | 2000 | 8.85 |
| 5 | 1000 | 8.67 |
| 6 | 00 | 6.65 |

Inference:

Trypsin is required for activation of influenza virus for inoculation of MDCK cells. From above results it is observed that, from 2000 to 3000 units of trypsin per roller bottle yields maximum virus potency.

Examples 5: Effect of Benzonase Concentration and Temperature on Cellular DNA Content and Virus Titre Different Concentrations of Benzonase were Tested to Degrade Host Cell DNA at Different Temperatures.

Clarified Virus Pool (CVP) was subjected to Benzonase treatment at concentrations 500 (with 2 mM $MgCl_2$), 500, 1000, 2500 and 5000 U/L and the treated CVPs were held at 32° C. for 3 hrs and further continued at 2-8° C. for overnight. Sampling was done at each stage and following are the results of DNA content at each stage.

TABLE 13

Influenza Strain: B/60/Phuket/2013/16 (Type B)
DNA content (ng/ml)

| Benzonase Concentration (U/L) | 3 Hrs at 32° C. | ON at 2-8° C. |
|---|---|---|
| Untreated | 4919 | 4919 |
| 500 (2 mM $MgCl_2$) | 13.75 | 7.6 |

TABLE 14

Influenza Strain: B/60/Phuket/2013/16 (Type B)
DNA content (ng/ml)

| Benzonase Concentration (U/L) | 3 Hrs at 32° C. | ON at 2-8° C. |
|---|---|---|
| Untreated | 4919 | 4919 |
| 500 | 353.6 | 22.45 |
| 1000 | 56.45 | 9.45 |
| 2500 | 11.3 | 9.15 |
| 5000 | 6.2 | 8.8 |

Inference:

From the results it was observed that CVP treated with benzonase concentration 500 U/L in presence of 2 mM $MgCl_2$ showed higher DNA degradation than the CVP treated with benzonase concentration 500 U/L without 2 mM $MgCl_2$. Also it is seen that higher benzonase concentrations 1000 U/L, 2500 U/L and 5000 U/L showed comparable DNA degradation with benzonase concentration 500 U/L (with 2 mM $MgCl_2$).

Examples 6: Virus Yield at Various Stages of Manufacturing

TABLE 15

Virus Yield at various Stages of Manufacturing

| | Titre ($EID_{50}$/0.5 ml) | | |
|---|---|---|---|
| Process Stage | Type A (H1N1) A/17/California/ 2009/38 | Type A (H3N2) A/17/Hong Kong/2014/8296 | Type B B/Texas/ 02/2013- CDC-LV8B |
| Harvest | 9.04 | 8.55 | 8.49 |
| Clarified Virus Pool (CVP) | 8.74 | 8.54 | 8.50 |
| Benzonase treated CVP | 8.63 | 8.42 | 8.22 |
| Virus Concentrate | 9.02 | 8.89 | 8.68 |
| Vaccine Bulk (CMVP) | 8.93 | 8.56 | 8.71 |

1. CVP: Clarified virus pool (harvest post filtration),
2. BCVP: CVP treated with Benzonase,
3. CMVP: Clarified monovalent virus pool (post TFF, addition of stabilizer and post 0.2µ filtration)

Inference:

Stage wise virus concentration was checked for each Type A (H1N1), Type A (H3N2) and Type B seasonal influenza viruses and it was observed that the initial virus concentration at harvest level was maintained throughout the process till the last stage i.e. preparation of vaccine bulk (CMVP).

TABLE 16

Mean Virus Recovery

| | | Harvest | | CMVP | | |
|---|---|---|---|---|---|---|
| Sr. No. | Strain | Virus Titer (Log EID50/0.5 ml) | Volume (ml) | Virus Titer (Log EID50/0.5 ml) | Volume (ml) | Recovery Percent (%) |
| 1 | A/17/Hongkong/2014/8296 | 8.29 | 10000 | 8.68 | 2500 | 61.37 |
| 2 | B/Texas/02/13-CDC-LV8B (Type B) | 8.49 | 8000 | 8.71 | 2300 | 47.71 |
| 3 | A/17/California/2009/38 | 9.04 | 10000 | 8.96 | 3000 | 24.95 |
| | % Mean Virus Recovery | | | | | 44.67 |

Inference:

Virus recovery can be calculated as percent virus retention during manufacturing where harvest is the starting point and CMVP is the end point of manufacturing. From the results it was can be concluded that the mean virus recovery is 44.67% which is equivalent to titer loss of 0.34 Log $EID_{50}$/0.5 ml. Also it is observed that the final virus recovery (virus titer) at CMVP level is within acceptable limit and the CMVP can be used to manufacture final product batches of MDCK based LAIV Virus.

Examples 7: Comparative Data of Stage Wise Host Cell DNA Concentration During Manufacturing of CMVP Clarified Virus Pool (CVP) of different strains were subjected to Benzonase treatment and stagewise sampling for DNA content was done. Following are the results of DNA content at each stage.

TABLE 17

Host cell DNA concentration (ng/ml)

| Sr. No. | Strain | Stagewise host cell DNA content (ng/ml) | | | |
|---|---|---|---|---|---|
| | | CVP | Benz-CVP | TFF Conc | CMVP |
| 1 | A/17/California/2009/38 | 4565 | 14.28 | 50.54 | 11.03 |
| 2 | A/17/Hongkong/2014/8296 | 5537 | 14.35 | 60.56 | 12.71 |
| 3 | B/60/Phuket/2013/16 (Type B) | 6467 | 10.45 | 31.12 | 3 |

Inference:

From the results it was observed that CVP when treated with benzonase showed significant reduction in DNA. And further it was observed that the residual DNA is again efficiently removed during the TFF process (diafiltration/concentration) and CMVP preparation process. The DNA content at final CMVP level ranges within the desired and acceptable limit.

Examples 8: Various Trials of TFF Experiments

Various TFF experiments were carried out with considerations of parameters like dilution medium used for TFF process (Virus Medium and PBS), diafiltration and concentration procedure. TFF concentrate samples were tested for virus concentration.

TABLE 18

TFF Experiments

| Experiment Code | TFF Process Parameters | | | | Virus Titre ($EID_{50}$/0.5 ml) | |
|---|---|---|---|---|---|---|
| | Dilution medium used | Diafiltration (DF) | Conc. (C) | Sequence of DF and conc. | Harvest Titre ($EID_{50}$/0.5 ml) | TFF Conc. Titre ($EID_{50}$/0.5 ml) |
| Expt. 1 (A/Cal) | VM | 3X | 4X | Conc. followed by DF | 8.94 | 8.07 |
| Expt. 2 (A/Cal) | VM | 3X | 4X | DF followed by conc. | 8.67 | 8.48 |
| Expt. 3 (A/Cal) | VM | — | 4X | Only conc. | 8.97 | 8.61 |
| Expt. 4 (B/Tex) | PBS | 2X | 4X | DF followed by conc. | 8.49 | 8.79 |
| Expt. 5 (A/HK) | PBS | 2X | 4X | DF followed by conc. | 8.79 | 8.83 |

A/Cal: A/17/California/2009/38;
B/Tex = B/Texas/02/2013-CDC-LV8B;
A/HK = A/17/Hong Kong/2014/8296;
VM: Virus medium Interpretation:

From above set of experiments the TFF process evolved and followed by 2×DF and 4× concentration stage were selected to get desired TFF concentrate with optimum virus yield. In comparison with VM, PBS gives better stability to the virus.

Examples 9: Immunogenicity Results

A study was undertaken to evaluate the performance of egg and MDCK cell culture based trivalent and quadrivalent seasonal influenza vaccines for immune response and efficacy of the vaccines in a ferret model. All animals were intranasally immunized on day 0 with egg and MDCK cell culture based trivalent or quadrivalent preparation containing strains similar to A/Michigan/45/2015 (H1N1), A/Hong Kong/4801/2015 (H3N2), B/Brisbane/60/2008 and B/Phuket/3073/2013 and challenged four weeks later (day 28).

TABLE 19

Geometricmean haemagglutination inhibition (HAI) and neutralization titers(NT) of sera collected on day 28

| Vaccine preparation | A/Michigan/45/2015 | | A/Hongkong/4801/2014 | | B/Brisbane/60/2008 | | B/Phuket/3073/2013 | |
|---|---|---|---|---|---|---|---|---|
| | HAI | NT | HAI | NT | HAI | NT | HAI | NT |
| Egg-based trivalent | 305 ± 76 | 222 ± 66 | 226 ± 84 | 323 ± 148 | 190 ± 69 | 150 ± 95 | 6 ± 1 | 12 ± 1 |
| Egg-based quadrivalent | 288 ± 87 | 183 ± 137 | 312 ± 90 | 527 ± 214 | 125 ± 32 | 162 ± 39 | 133 ± 40 | 323 ± 114 |
| MDCK-based trivalent | 411 ± 114 | 415 ± 185 | 452 ± 71 | 725 ± 192 | 315 ± 74 | 333 ± 112 | 5 ± 0 | 12 ± 0 |
| MDCK-based quadrivalent | 234 ± 70 | 140 ± 72 | 214 ± 108 | 304 ± 236 | 152 ± 49 | 148 ± 77 | 134 ± 37 | 256 ± 78 |
| Placebo | 10 ± 2 | 13 ± 1 | 5 ± 0 | 13 ± 1 | 5 ± 0 | 12 ± 0 | 6 ± 1 | 12 ± 1 |

Figure 12:
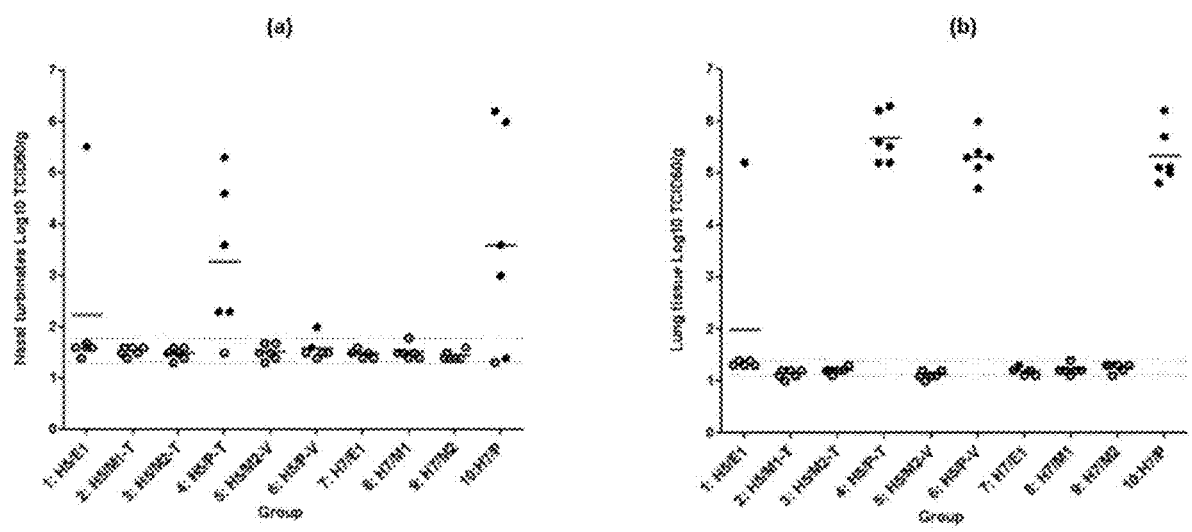
FIG. 12: Infective virus testing in the nasal turbinate and lung samples. Animals were vaccinated with one or two doses of H5 LAIV, H7 LAIV or placebo. Groups 1 to 4 were challenged with H5/tk/Tk, groups 5 and 6 challenged with H5/Vt and groups 7 to 10 challenged with H7/An. Nasal turbinate samples (a) and lung samples (b) collected on day 4 post infection were titrated for the presence of replication competent virus particles. Individual titres are shown with group mean indicated by a solid black line.
Figure 13:
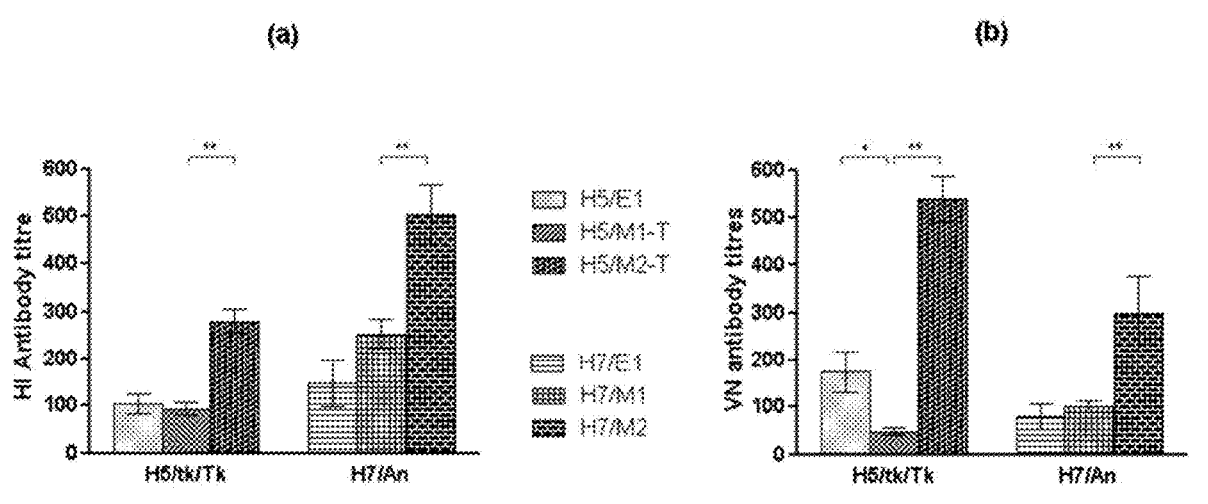

Inference: (Refer FIGS. 12 & 13)

It was concluded that vaccination with egg based and MDCK based trivalent and quadrivalent vaccines containing A-H1N1 can protect the animals against A-H1N1 infection when challenged with homologous A-H1N1 viruses.

Another study was undertaken to evaluate the performance of both egg and MDCK cell based monovalent LAIVs (A-H5N2 and A-H7N9) for immune response and efficacy in a ferret model. Different groups of animals were immunized with egg and MDCK cell culture based A-H5N1 and A-H7N9 monovalent LAIVs and challenged with homologous A-H5N1 and A-H7N9 viruses respectively. The results had shown that animals immunized with monovalent H5N2 LAIV were protected against homologous challenge with A-H5N1 virus. Animals immunized with monovalent A-H7N9 LAIV were protected against homologous challenge with A-H7N9 virus.

We claim:

1. An immunogenic composition comprising:

a) one or more Influenza viruses at a dose of 6 to 7 Log $EID_{50}$ per 0.5 ml; and b) a stabilizer composition comprising;

i. 1 to 10% (w/v) sucrose;

ii. 0.1% to 2% (w/v) of histidine;

iii. 0.01% to 1% (w/v) alanine;

iv. 0.1% to 2% (w/v) tricine;

v. 0.1 to 5% (w/v) arginine; and vi. 0.1 to 5% (w/v) gelatin.

2. The immunogenic composition as claimed in claim 1, wherein the influenza virus comprise of pandemic or seasonal Influenza virus, a live attenuated influenza vaccine (LAIV) virus, an inactivated influenza virus, a chimeric influenza virus, or a recombinant influenza virus.

3. The immunogenic composition as claimed in claim 1, wherein composition is monovalent in terms of Influenza virus derived from Influenza type A or type B or type C or its subtypes.

4. The immunogenic composition as claimed in claim 1, wherein composition is multivalent in terms of Influenza virus derived from Influenza type A or type B or type C or its subtypes.

5. The immunogenic composition as claimed in claim 1, wherein Influenza virus are reassortant LAIV virus comprising cold adapted, temperature sensitive and/or attenuated phenotype gene segments of master donor viruses (MDVs) and haemagglutinin (HA) and/or neuraminidase (NA) gene segments of the wild type pandemic or seasonal influenza type A or B or C virus strains in a ratio of 1:7, 2:6, 3:5, 4:4, 5:3, 6:2 or 7:1.

6. The immunogenic composition as claimed in claim 5, wherein master donor virus (MDVs) is selected from the group comprising of A/Leningrad/134/17/57 (H2N2) Influenza A strain, B/USSR/60/69 Influenza B strain.

7. The immunogenic composition as claimed in claim 5, wherein the reassortant LAIV virus comprise of the haemagglutinin (HA) gene and/or neuraminidase (NA) gene from the influenza A virus or H1 to H18 and N1 to N11 and its subtypes H1N1, H2N2, H3N2, H5N1, H5N3, H9N2, H7N1, H7N3, H7N7, H6N1, H7N9, or H10N8.

8. The immunogenic composition as claimed in claim 5, wherein the reassortant LAIV virus comprise of the haemagglutinin (HA) gene and/or neuraminidase (NA) gene from the influenza A virus strain pdmH1N1 strain—A/California/07/2009 (referred to as A/Cal)-like strain or A/Cal, A/Michigan/45/2015-like strain, A/South-Africa/3626/2013 like strain, or H3N2-A/Hong Kong/4801/2014-like strain.

9. The immunogenic composition as claimed in claim 5, wherein the reassortant LAIV virus comprise of the haemagglutinin (HA) gene and/or neuraminidase (NA) gene from the influenza B virus strain Victoria lineage-B/Brisbane/60/2008-like strain or Yamagata lineage-B/Phuket/3073/2013-like strain.

10. The immunogenic composition as claimed in claim 1, wherein the composition additionally comprises an adjuvant selected from the group of aluminum hydroxide, aluminum phosphate, aluminum hydroxyphosphate, and potassium aluminum sulfate or a mixture thereof.

11. The immunogenic composition as claimed in claim 1, wherein the single dose composition is free of preservative and the multi-dose composition comprises of one or more preservative selected from the group of 2-phenoxyethanol, Benzethonium chloride (Phemerol), Phenol, Thiomersal, Formaldehyde, methylparaben, propylparaben, benzyl alcohol or a combination thereof.

12. The immunogenic composition as claimed in claim 1, wherein the composition comprises of a buffer selected from sodium chloride, carbonate, citrate, lactate, gluconate, tartrate, phosphate buffer saline, HEPES, Citrate-phosphate or TRIS.

13. The immunogenic composition as claimed in claim 1, wherein the composition comprises of a pharmaceutically acceptable transporter, excipient, binder, carrier, isotonic agent, emulsifier or humectant.

14. The immunogenic composition as claimed in claim 13, wherein the composition comprises a pharmaceutically acceptable excipient selected from the group of sugars, polyols, salts including NaCl, KCl, $KH_2PO_4$, $Na_2HPO_4 \cdot 2H_2O$, $CaCl_2$, or $MgCl_2$, aminoacids or pH modifiers.

15. The immunogenic composition as claimed in claim 1, wherein the final pH of the immunogenic composition comprises of pH 6.5 to 8.

16. The immunogenic composition as claimed in claim 1, wherein the Influenza type B virus is present at a dose of 6 to 7 Log $EID_{50}$ per 0.5 ml; more preferably NLT 6.5 Log $EID_{50}$ per 0.5 ml.

17. The immunogenic composition as claimed in claim 1, prepared via a method that comprises the following steps:
   a) Infecting Madin Darby canine kidney (MDCK) Cell (ATCC CCL-34) culture host with Influenza virus at a MOI between 1:100 to 1:10000
   b) Harvesting of Supernatant comprising Influenza virus post incubation period of 40 to 70 hrs in MEM containing trypsin in the range of 5 to 25U/ml;
   c) Filtering the viral harvest by direct flow filtration (DFF) through at least one clarification filter having a pore size of between about 6 micrometers to about 0.45 micrometers;
   d) Treating the CVP with Benzonase having concentration in range of 0.5 units/ml to 5 units/ml in presence of a divalent cation $Mg^{2+}$ salt at concentration of 1 to 3 mM, at temperature ranging in between 30-34° C. for 2 to 6 hours and subsequently at temperature of 2 to 8° C. for 5 to 15 hours;
   e) Concentrating Benzonase treated CVP by tangential flow filtration (TFF) using a membrane with a molecular weight cut off (MWCO) of 100 KDa-500 KDa resulting in at least 4× concentration of viral harvest;
   f) Stabilizing the TFF concentrate with a stabilizer composition comprising one or more carbohydrate, one or more amino-acid and gelatin to form a stabilized viral harvest;
   g) Sterilizing the stabilized TFF concentrate by DFF through at least one sterilization grade filter having a pore size of between about 0.8 micrometers to about 0.2 micrometers to form a sterilized CMVP;
      wherein the overall recovery of purified viruses is more than or equal to 40%.

18. The immunogenic composition as claimed in claim 1, wherein the immunogenic composition is formulated for a human subject using one of intranasal, intramuscular, intravenous, subcutaneous, transcutaneous or intradermal route; and wherein the immunogenic composition is formulated as single dose vials or multidose vials or multidose kit or as pre-filled syringes or nasal sprays for reducing the onset of or preventing a health condition comprising Influenza A virus infection or its subtypes, Influenza B virus infection or its subtypes or Influenza C virus infection or its subtypes.

19. The immunogenic composition as claimed in claim 1, wherein the composition comprises:
   a) One or more live attenuated Influenza vaccine (LAIV) virus at a dose of 6 to 7 Log $EID_{50}$ per 0.5 ml;
   b) Sucrose 3 to 6% (w/v);
   c) Histidine 0.1% to 1% (w/v);
   d) Alanine 0.05% to 0.5% (w/v);
   e) Tricine 0.1% to 0.5% (w/v);
   f) Arginine 0.1 to 3% (w/v); and
   g) Gelatin 0.1 to 3% (w/v).

20. The immunogenic composition as claimed in claim 1, wherein the composition comprises:
   a) One or more live attenuated Influenza vaccine (LAIV) virus at a dose of 6 to 7 Log $EID_{50}$ per 0.5 ml;
   b) Sucrose 4% (w/v);
   c) Histidine 0.21% (w/v);
   d) Alanine 0.1% (w/v);
   e) Tricine 0.3% (w/v);
   f) Arginine 2.1% (w/v); and
   g) Gelatin 0.85% (w/v).

21. The immunogenic composition as claimed in claim 1, wherein the composition comprises:
   a) One or more live attenuated Influenza vaccine (LAIV) virus NLT at a dose of 6 to 7 Log $EID_{50}$ per 0.5 ml;
   b) Sucrose 4% (w/v);
   c) Histidine 0.21% (w/v);
   d) Alanine 0.1% (w/v);
   e) Tricine 0.3% (w/v);
   f) Arginine 2.1% (w/v); and
   g) Gelatin 1% (w/v).

22. The immunogenic composition as claimed in claim 1, wherein the composition comprises:
   a) One or more live attenuated Influenza vaccine (LAIV) virus at a dose of 6 to 7 Log $EID_{50}$ per 0.5 ml;
   b) Sucrose 4% (w/v);
   c) Histidine 0.21% (w/v);
   d) Alanine 0.1% (w/v);
   e) Tricine 0.3% (w/v);
   f) Arginine 1.6% (w/v); and
   g) Gelatin 1% (w/v).

* * * * *